(12) United States Patent  (10) Patent No.: US 7,183,534 B2
Hisano                     (45) Date of Patent:     Feb. 27, 2007

(54) PHOTODETECTOR, METHOD OF USING THE SAME, AND IMAGE FORMING APPARATUS

(75) Inventor: Tohru Hisano, Kanagawa (JP)

(73) Assignee: Fuji Xerox Co., Ltd, Tokyo (JP)

( * ) Notice: Subject to any disclaimer, the term of this patent is extended or adjusted under 35 U.S.C. 154(b) by 302 days.

(21) Appl. No.: 10/377,643

(22) Filed: Mar. 4, 2003

(65) Prior Publication Data

US 2004/0056264 A1   Mar. 25, 2004

(30) Foreign Application Priority Data

Sep. 20, 2002  (JP) ............ P2002-275212

(51) Int. Cl.
*G01N 21/47* (2006.01)
*G01J 1/10* (2006.01)

(52) U.S. Cl. ............ 250/227.11; 250/216; 250/559.16; 356/342

(58) Field of Classification Search .......... 257/79–103, 257/431–437; 250/573; 399/27, 29
See application file for complete search history.

(56) References Cited

U.S. PATENT DOCUMENTS 3,842,263 A * 10/1974 Kornrumpf et al. ........ 250/239

4,796,065 A * 1/1989 Kanbayashi ................. 399/60
5,218,212 A * 6/1993 Sato et al. ................... 250/573
6,583,444 B2 * 6/2003 Fjelstad ....................... 257/82

FOREIGN PATENT DOCUMENTS

| JP | 6-175501  | 6/1994 |
| JP | 7-177091  | 7/1995 |
| JP | 2002-98637 | 4/2002 |

OTHER PUBLICATIONS

Merriam-Webster's Collegiate Dictionary, tenth Edition, 1999 (p. 1079), Merriam-Webster, Incorporated, Springfield, Massachusetts, USA.*
J.D. Jackson, "Classical Electrodynamics", John Wiley & Sons, New York, sixth edition (1967), pp. 220-221.*

* cited by examiner

*Primary Examiner*—Johannes Mondt
(74) *Attorney, Agent, or Firm*—Morgan, Lewis & Bockius, LLP

(57) ABSTRACT

A photodetector includes a light emitting portion for applying light, a light receiving portion for sensing the light, and a light guiding member 3 for guiding the light from the light emitting portion to a surface to be measured and guiding detection light from the surface to be measured to the light receiving portion. The light guiding member has a sheet-like optical transmission medium, which is disposed at a portion facing to the surface to be measured and transmits the light by internal reflection. The sheet-like optical transmission member has an optical aperture facing to the surface to be measured.

9 Claims, 22 Drawing Sheets

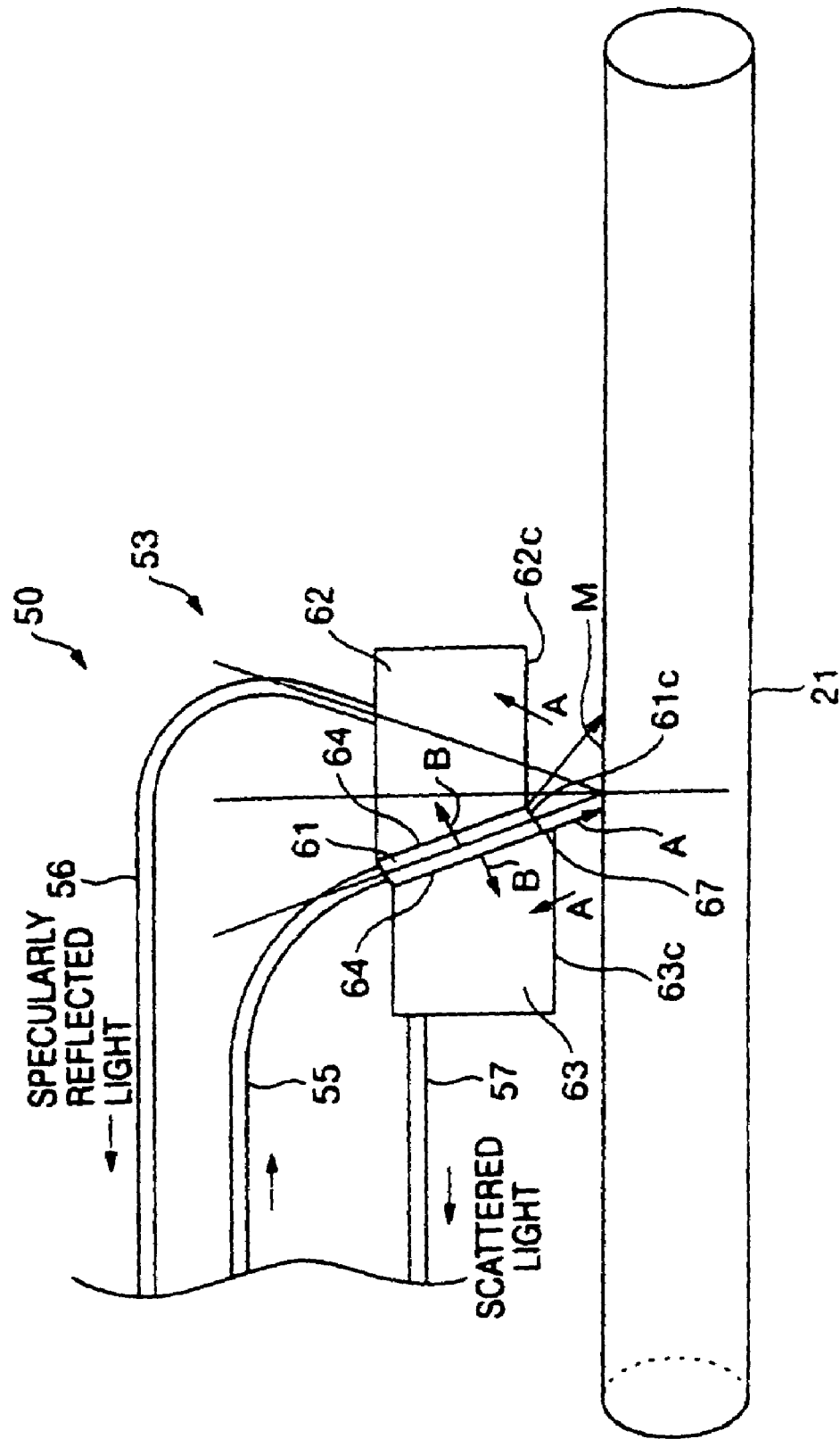

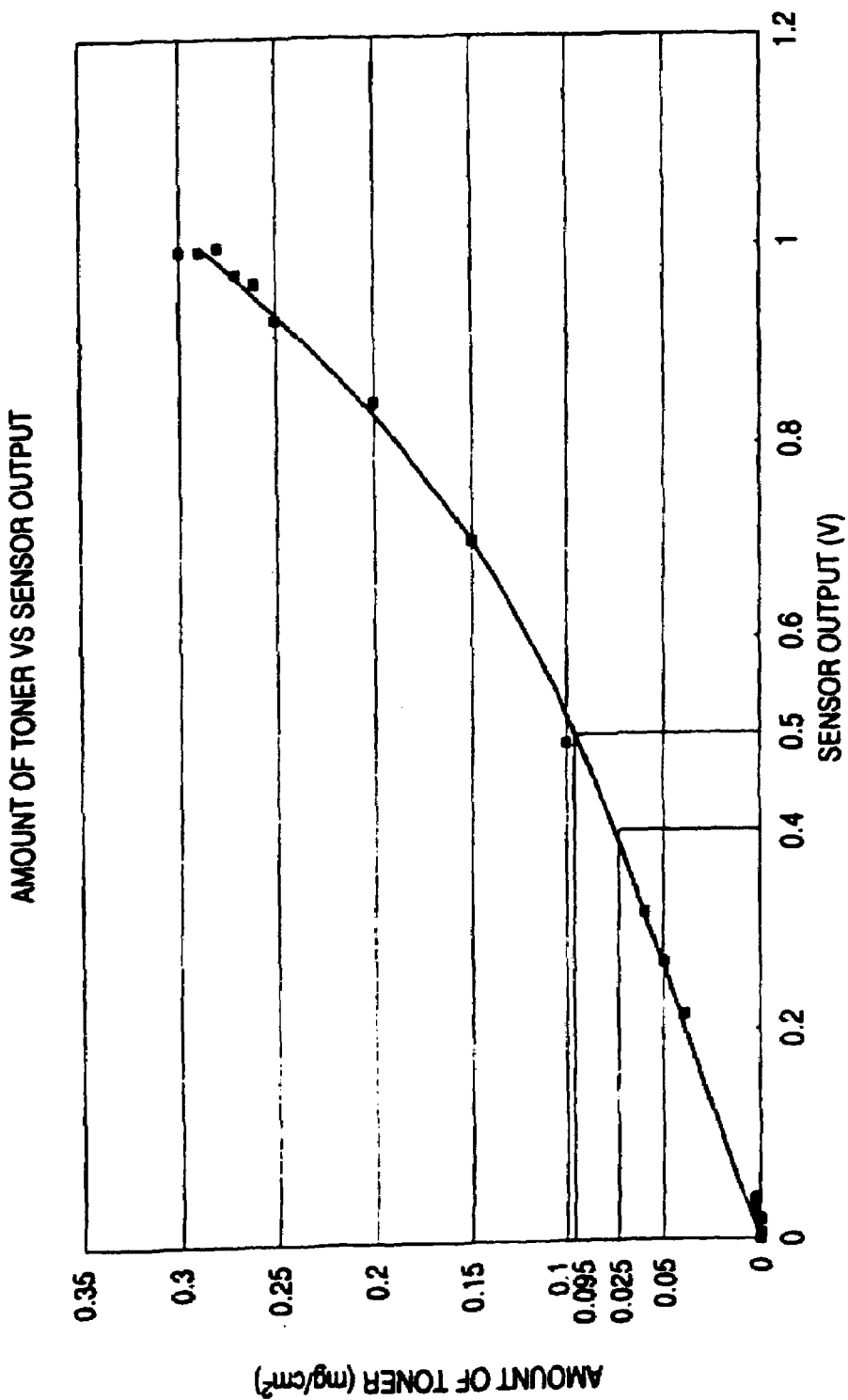

PHOTODETECTOR, METHOD OF USING THE SAME, AND IMAGE FORMING APPARATUS

The present disclosure relates to the subject matter contained in Japanese Patent Application No. 2002-275212 filed on Sep. 20, 2002, which is incorporated herein by reference in its entirety.

BACKGROUND OF THE INVENTION

1. Field of the Invention

The present invention relates to a photodetector for detecting optical information from a surface to be measured, and more particularly to improvements in a photodetector having a form for guiding light from a light emitting portion to a surface to be measured through a light guiding member and for guiding the detected light from the surface to be measured to a light receiving portion through the light guiding member, as well as a method of using the same, and an image forming apparatus using the same.

2. Description of the Related Art

Generally, photodetectors are arranged to detect optical information from a surface to be measured by applying light to the surface to be measured, and has been widely used in various fields.

For example, in an image forming apparatus such as a copying machine, a printer, and a facsimile equipment, adopting the electrophotographic system, a system is adopted in which a toner patch for density detection is formed on an image carrying body such as a photoconductor or an intermediate transfer member, and the photodetector (here, a toner amount detector) detects the amount of toner of the toner patch to perform image density control.

Here, a description will be given of general toner amount detectors, and there are the following two systems.

The first system is called a reflected-light detection system, and utilizes the fact that the surface of the image carrying body such as the photoconductor or an intermediate transfer member to which the toner adheres has a mirror surface structure having a high degree of flatness.

Namely, as shown in FIG. 19A, in this reflected-light detection system, light of a fixed intensity is applied from a light source 201 to a surface of an image carrying body 200, a photodiode 202, i.e., a light receiving element receives specularly reflected light thereof to convert the received light into a voltage corresponding to its intensity (see JP-A-6-175501).

At this time, the reflected light scatters at portions where a toner 203, which is a surface to be measured, adheres, and the quantity of light declines by that portion. Therefore, the output voltage drops at the portion where the quantity of light declines.

Consequently, relationship between the amount of toner and the output voltage is obtained as shown in FIG. 19B. The toner amount detection in the image forming apparatus becomes possible.

However, with this reflected-light detection system, if the surface of the image carrying body is substantially covered with the toner, it becomes impossible to obtain reflected light, rendering the detection impossible. Accordingly, with this reflected-light detection system, the toner amount detection is possible in an area where the toner adheres to the image carrying body by a very small amount or by about one layer.

In addition, the second system is called a scattered-light detection system, and is used in the case of a color toner, for example.

Namely, as shown in FIG. 20A, this scattered-light detection system utilizes the characteristic that if the light from a light source 211 is applied to a color toner 213 on the image carrying body 200, scattered light occurs due to the surface reflection and internal reflection. A photodiode 212, i.e., a light receiving element, is disposed at a portion other than a light receiving portion for receiving the specularly reflected light, and the aforementioned scattered light is monitored by this photodiode 212.

In the case of this system, as shown in FIG. 20B, as the amount of toner increases, the output voltage of the photodiode 212 changes in such a manner as to rise, thereby permitting the toner amount detection.

In this scattered-light detection system, even in a case where a plurality of layers of toner adhere to the image carrying body 200, the scattered light from the lower layer toner transmits through the surface layer toner and returns. For this reason, this scattered-light detection system can obtain an output even with respect to a greater amount of toner than that in the reflected-light detection system.

However, the scattered-light detected system cannot be applied to a black toner, which does not cause scattered light.

Each of the toner amount detectors (photodetectors) of these two systems includes a light source, lenses, a light receiving element, a drive circuit board, and the like. These constituent members are frequently arranged integrally and are disposed in the vicinity of a measuring point.

For this reason, the toner amount detector is generally disposed at a position distant from the measuring point by several millimeters to 10-odd millimeters and with a thickness and a width ranging from about 5 mm to about 15 mm.

At this time, the principal factor for restraining the size of the sensor (toner amount detector) is derived from need to dispose the optical system, the elements, and circuits concerning the measurement in the vicinity of the measuring point.

In view of the requirement of the illuminating optical system, if the distance between the light source and the light emitting element (light source) is made long, electromagnetic noise becomes liable to affect the system, making it difficult to ensure stability in the quantity of illuminating light.

In addition, in view of the requirement of the receiving optical system, an extremely weak current generated by the light receiving element needs to be amplified at a position as close to the light receiving element as possible so as to obtain a stable analog signal. For this reason, the light receiving element is often directly connected to the drive circuit board in the vicinity of the measurement position.

Further, the light emitting element and the light receiving element have millimeter of externals shapes, with the result that the sensor is provided with the above-described size.

Since this type of toner amount detector (sensor) is disposed in the vicinity of the measuring point, it is naturally necessary to secure an installation space for the sensor in the vicinity of the measuring point.

In recent years, however, in the light of demand for making the image forming apparatuses compact, various sub units tend to be arranged with high densities inside the image forming apparatuses.

For example, so-called tandem-type image forming engines in which four image forming units are arranged for forming toner images of various color components are becoming a mainstream.

In the case of such an apparatus, it is often impossible to obtain a space, which allows the sensor to be disposed in the vicinity of the position subject to measurement.

Since the amount of toner to be essentially detected cannot be detected in this case, the actual situation is such that it is inevitable to adopt a technique whereby process control is performed after the amount of toner is estimated from a substitute value.

In contrast, JP-A-7-177091 shows that the communication of main digital signals in an image forming apparatus including a toner amount detector and the like is effected by using optical fibers.

If this system is used, it is possible to alleviate the effect due to the electromagnetic noise of the signal.

If such a conventional technique is used, it is proposed that optical fibers are used to propagate an analog quantity of light, which the toner amount detector handles, as shown in JP-A-2002-98637, for example.

For example, as shown in FIG. 21, light from a light source 221 is led to a measuring point P by using an incident-side optical fiber 222. Detected light from the measuring point P is led to an output-side optical fiber 224 through a focusing lens 223 and is led to a light receiving element 225 such as a photodiode by using this output-side optical fiber 224.

In accordance with this form, it theoretically becomes possible to dispose the light source 221 and the measuring point P as well as the measuring point P and the light receiving element 225 in such a manner as to be spaced apart from each other.

In addition, only the optical fibers 222 and 224 and the focusing lens 223 are disposed in the vicinity of the measuring point P. Therefore, it becomes possible to realize a substantially compact sensor (toner amount detector) correspondingly.

Accordingly, even if the installation space in the vicinity of the measuring point P is narrow, it becomes possible to dispose the sensor efficiently.

However, with this type of toner amount detector, the following technical problems have been encountered.

First, with the above-described toner amount detector, the detected light from a spot-like measuring point P must be focused. Therefore, if the surface to be measured, which constitutes the measuring point P, becomes deteriorated, not only is the deterioration of the surface to be measured liable to immediately affect the detection accuracy, but the detected light from the measuring point P is difficult to be reliably focused onto the output-side optical fiber 224. At any rate, there is a technical problem in that the deterioration of the surface to be measured is liable to result in a decline in the detection accuracy.

In addition, although this type of toner amount detector uses optical fibers, the transmittance of the optical fiber is likely to vary due to a change in its shape and the like. For this reason, it is difficult to propagate the analog quantity of light stably.

Here, it is possible to cite the following as factors for the variation of the transmittance.

due to thermal expansion and a change in shape
due to contamination at a junction
a decline in the transmittance over time The effect of the variation of the transmittance on the detection accuracy will be examined. If it is now assumed that monitoring is performed in accordance with the reflected-light detection system by using the toner amount detector shown in FIG. 21, results shown in FIG. 22 are obtained.

At this time, if it is assumed that the transmittance has declined by, for example, 10%, it can be understood that the amount of toner measured which should be, for example, 0.095 mg/cm$^2$ is erroneously measured to be 0.075 mg/cm$^2$.

In such a situation, it is assumed that the measurement accuracy required is assumed to be about 0.01 mg/cm$^2$. This portion alone of the variation of the quantity of light produces an amount of fluctuation, which is twice as large as a target value, causing a decline in the detection accuracy.

SUMMARY OF THE INVENTION

The present invention has been devised to overcome the above-described technical problems. An object of the invention is to provide a photodetector for effectively preventing a decline in detection accuracy in a form in which a light guiding member is used between a light emitting portion and a light receiving portion, as well as a method of using the photodetector and an image forming apparatus using the same.

According to an aspect of the invention, there is provided a photodetector for detecting at least one of light reflected or scattered from a surface to be measured. The photodetector includes a light emitting portion, a light receiving portion, and a light guiding member. The light emitting portion emits light. The light receiving portion senses light. The light guiding member guides the light from the light emitting portion to the surface to be measured and guides detection light from the surface to be measured to the light receiving portion. The light guiding member has a sheet-like optical transmission medium disposed at a portion facing to the surface to be measured and transmits the light by internal reflection and including an optical aperture opposite to the surface to be measured.

BRIEF DESCRIPTION OF THE DRAWINGS

FIG. 9 is an explanatory diagram illustrating an outline of the photodetector in accordance with a fourth embodiment;

FIG. 22 is an explanatory diagram illustrating sensor output characteristics of the photodetector shown in FIG. 21.

DETAILED DESCRIPTION OF PREFERRED EMBODIMENTS

Figure 1A:
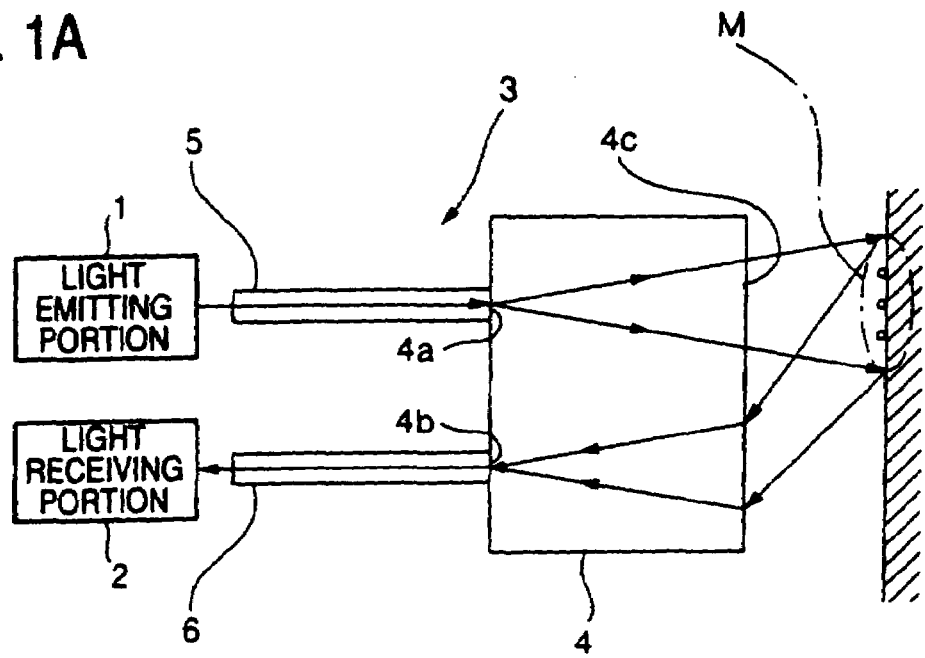
FIG. 1A is an explanatory diagram illustrating an outline of a photodetector in accordance with the invention.

Namely, as shown in FIG. 1A, there is provided a photodetector for detecting at least one of light reflected or scattered from a surface to be measured M. The photodetector includes a light emitting portion 1, a light receiving portion 2, and a light guiding member 3. The light emitting portion 2 emits light. The light receiving portion 2 senses light. The light guiding member 3 guides the light from the light emitting portion 1 to the surface to be measured M and guides detection light from the surface to be measured M to the light receiving portion 2. The light guiding member 3 has a sheet-like optical transmission medium 4 disposed at a portion facing to the surface to be measured M and transmits the light by internal reflection, and including an optical aperture 4c facing to the surface to be measured M.

In such a technique, the photodetector has as an object to be detected either one of reflected light and scattered light.

Further, the light guiding member 3 may be selected from a wide range of members including an optical fiber so long as the member applies the light from the light emitting portion 1 to the surface to be measured M and guides the detected light from the surface to be measured M.

Further, the sheet-like optical transmission medium 4 may be of a single-layered structure or a multi-layered structure so long as the sheet-like optical transmission medium 4 is shaped in sheet form and conducts optical transmission by internal reflection.

Furthermore, although the sheet-like optical transmission medium 4 has the optical aperture 4c facing to the surface to be measured M, the optical aperture referred to herein may be appropriately selected so long as the optical aperture has functions capable of applying predetermined light to the surface to be measured M and receiving the detected light from the surface to be measured M.

In addition, in the form shown in FIG. 1A, since the sheet-like optical transmission medium 4 has an elongated optical aperture 4c, the sheet-like optical transmission medium 4 makes it possible to secure the surface to be measured M widely and facilitates the focusing of the detected light from the surface to be measured M.

Furthermore, since the sheet-like optical transmission medium 4 can be installed in a narrow installation space, the degree of freedom of the installation place is high.

In addition, in the invention, the light guiding member 3 is sufficient if the light guiding member 3 has at least the sheet-like optical transmission medium 4. However, as a typical form of the light guiding member 3, the light guiding member includes an incident-side optical transmission member 5 and an output-side optical transmission member 6. The incident-side optical transmission member 5 forms an optical transmission path between the light emitting portion 1 and an incident portion 4a of the sheet-like optical transmission medium 4. The output-side optical transmission member 6 forms an optical transmission path between an output portion 4b of the sheet-like optical transmission medium 4 and the light receiving portion 2.

According to this form, the positional relationship among the light emitting portion 1, the light receiving portion 2, and the sheet-like optical transmission medium 4 can be set in a spaced-apart relation. As a result, it is possible to enhance the degree of freedom in the layout.

In addition, as the incident-side optical transmission member 5 and the output-side optical transmission member 6, optical fibers or the like, which can be bent, are preferable.

Further, as another form of the sheet-like optical transmission medium 4, there is a form in which the above-described optical transmission members 5 and 6 are not used.

For example, an incident-side optical transmission portion for guiding the light from the light emitting portion 1 and an output-side optical transmission portion for guiding the light to the light receiving portion 2 may be integrally provided on the sheet-like optical transmission medium 4.

Further, the sheet-like optical transmission medium 4 may be formed of a single member or may be formed of a plurality of members.

In the former case, the sheet-like optical transmission medium 4 may include a light applying portion for applying the light to the surface to be measured M and a light detecting portion for detecting the light from the surface to be measured M as the optical aperture. The sheet-like optical transmission medium is a single sheet-like optical transmission medium.

In the latter case, the sheet-like optical transmission medium 4 may include a light applying portion for applying the light to the surface to be measured M and a light detecting portion for detecting the light from the surface to be measured M as the optical aperture. The sheet-like optical transmission medium is a plurality of sheet-like optical transmission media. The light applying portion is formed in the different sheet-like optical transmission medium from the light detecting portion.

In addition, in this form, when the photodetector is configured as the reflected-light detection system, the sheet-like optical transmission medium 4 suffices so long as the sheet-like optical transmission medium 4 includes a light applying portion for applying the light to the surface to be measured M and a light detecting portion for detecting the light from the surface to be measured M as the optical aperture 4c, and the optical detecting portion allows specularly reflected light from the surface to be measured M to be incident thereon.

Meanwhile, in a case where the photodetector is configured as the scattered-light detection system, the sheet-like optical transmission member 4 suffices so long as the sheet-like optical transmission medium 4 includes a light applying portion for applying the light to the surface to be measured M and a light detecting portion for detecting the light from the surface to be measured M as the optical aperture 4c, and the light detecting portion does not allow specularly reflected light from the surface to be measured M to be incident thereon and allows scattered light from the surface to be measured M to be incident thereon.

At this time, when the photodetector is configured as the scattered-light detection system, as a preferred example of the layout of the optical aperture 4c, the sheet-like optical transmission member 4 suffices so long as the sheet-like optical transmission medium 4 is arranged so that the light applying portion for applying the light to the surface to be measured M and the light detecting portion for detecting the light from the surface to be measured M are spaced apart from each other.

If the light applying portion and the light detecting portion are disposed in such a manner as to spaced apart from each other, it becomes possible to prevent the incidence of the specularly reflected light upon the light detecting portion.

Furthermore, when the photodetector is configured as the scattered-light detection system, as a preferred example of the construction of the optical aperture 4c, the sheet-like optical transmission member 4 suffices so long as the sheet-like optical transmission medium 4 has a light shielding wall around the light applying portion for applying the light to the surface to be measured M.

By providing the light shielding wall in this manner, it becomes possible to prevent the incidence of the specularly reflected light upon the light detecting portion.

In addition, as for an example of the layout in the light transmitting direction of the sheet-like optical transmission medium 4, the incident portion on which the light from the light emitting portion 1 is incident and the output portion from which the light is output to the light receiving portion 2 may be formed at a portion substantially parallel to the optical aperture facing to the surface to be measured M. Alternatively, the incident portion on which the light from the light emitting portion 1 is incident and the output portion from which the light is output to the light receiving portion 2 may be formed at a portion substantially perpendicular to the optical aperture 4c facing to the surface to be measured M.

Figure 1B:
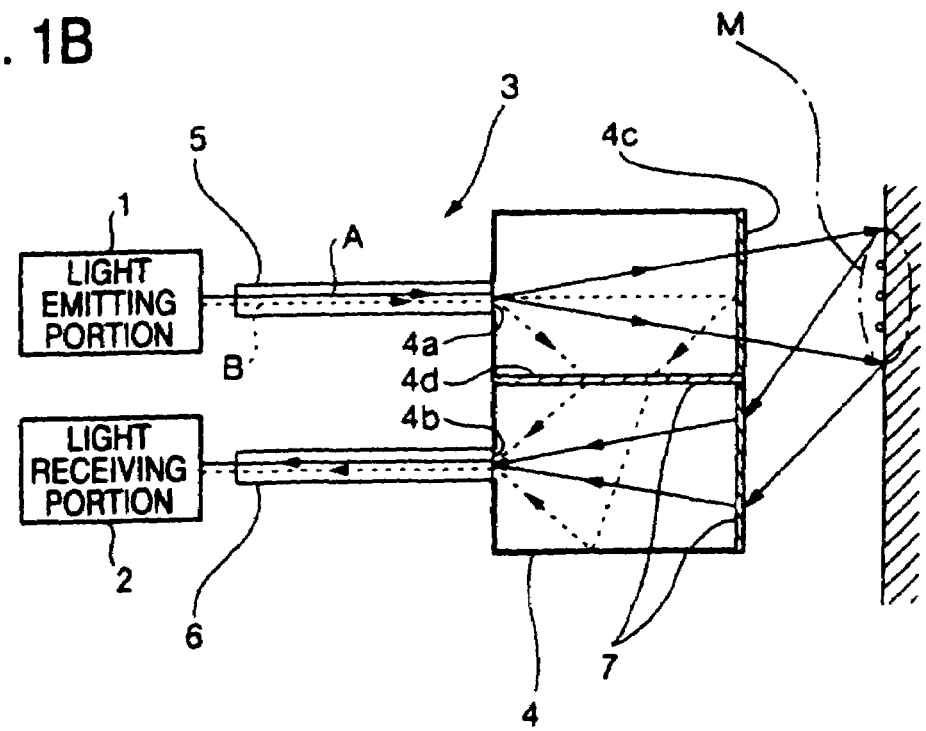
FIG. 1B is an explanatory diagram illustrating another form of the photodetector in accordance with the invention.

In addition, in another form of the invention, as shown in FIG. 1B, there is provided a photodetector for detecting light reflected or scattered from a surface to be measured M. The photodetector includes a light emitting portion 1, a light receiving portion 2, and a light guiding member 3. The light emitting portion 1 emits the light of two kinds of different wavelengths A, B. The light receiving portion 2 senses the light of the two kinds of different wavelengths A, B. The light guiding member 3 includes an optical-transmission-path separating member 7 applyies one of the light of the two kinds A from the emitting portion 1 to the surface to be measured M and guiding detection light from the surface to be measured M together with the other of light of the two kinds B to the light receiving portion 2.

This form specifically describes the photodetector corresponding to a dual-wavelength beam system, and the sheet-like optical transmission medium 4 is not necessarily essential.

For this reason, in the form in which the sheet-like optical transmission medium 4 is not provided, a form may be included in which the optical-transmission-path separating member 7 is provided as a part of the light guiding member 3.

According to this form, by the optical-transmission-path separating member 7, "the detection light from the surface to be measured M+the component of variation of the transmittance of the light guiding member 3" can be detected from the light of one wavelength, while "the component of variation of the transmittance of the light guiding member 3" can be detected from the light of the other wavelength. Therefore, by canceling the component of variation of the transmittance of the light guiding member 3, it is possible to detect only the detected light from the surface to be measured M.

In addition, as a typical form of the photodetector corresponding to the dual-wavelength beam system, the light guiding member 3 is disposed at a portion facing to the surface to be measured M. The light guiding member 3 includes a sheet-like optical transmission medium 4, which transmits the light by inside reflection and has an optical aperture 4c facing to the surface to be measured M. The light transmission path separating member 7 is disposed in the sheet-like optical transmission medium 4. The optical-transmission-path separating member 7 applies one of the light of the two kinds (for example, light of wavelength A) through the optical aperture 4c to the surface to be measured M, fetches reflected or scattered light from the surface to be measured M, and does not apply the other of the light of the two kinds (for example, light of wavelength B) through the optical aperture 4c to external.

Thus, this arrangement is preferable since the use of the sheet-like optical transmission medium 4 makes it possible to secure the surface to be measured M widely and permits the installation even if the space in the vicinity of the surface to be measured M is narrow.

Furthermore, in the form shown in FIG. 1B, the light guiding member 3 may include an incident-side optical transmission member 5 and an output-side optical transmission member 6. The incident-side optical transmission member 5 guides the light of the two kinds A, B from the light emitting portion 1 to an incident portion 4a of the sheet-like optical transmission medium 4. The output-side optical transmission member 6 guides the light of the two kinds A, B output from an output portion 4b of the sheet-like optical transmission medium 4 to corresponding sensing portions of the light receiving portion 2, respectively.

In this form, the incident-side optical transmission member 5 includes, for instance, an optical fiber which can be freely bent and a light combining member whereby light rays applied from a plurality of directions of the light emitting portion 1 are combined in one direction.

Meanwhile, the output-side optical transmission member 6 includes, for instance, an optical fiber which can be freely bent and a light separating member whereby the light in one direction is separated into a plurality of directions toward the light receiving portion 2.

In addition, as a typical form of the optical-transmission-path separating member 7, the optical aperture 4c is coated with reflection coating having wavelength dependency. The one of the light of the two kinds (for example, A) can transmit the reflection coating. The other of the light of the two kinds (for example, B) can be reflected at the reflection coating.

Further, as a typical form of the optical-transmission-path separating member 7 in a case where the sheet-like optical transmission medium 4 is formed of a plurality of members, the sheet-like optical transmission medium 4 includes a light applying portion for applying the light to the surface to be measured M and a light detecting portion for detecting the light from the surface to be measured M as the optical aperture 4c. The sheet-like optical transmission medium 4 is a plurality of sheet-like optical transmission media. The light applying portion is formed in the different sheet-like optical transmission medium from the light detecting portion. A junction 4d between the plurality of sheet-like optical transmission media 4 is coated with reflection coating. The one of the light of the two kinds (for example, A) can be reflected at the reflection coating. The other of the light of the two kinds (for example, B) can transmit the reflection coating.

In addition, as a preferable method of using the photodetector shown in, for example, FIG. 1A, it is possible to cite the following method: In an image forming apparatus for forming a visible image using a colorant on an image carrying body at the time of using the photodetector shown in FIG. 1A as a device for detecting an amount of the colorant of the visible image on the image carrying body, a result of photodetection is determined on the basis of information S(t) in which arithmetic processing is effected in accordance with $$S(t) = \{V \max - V(t)\} / \{V \max - V \min\}$$

where V(t) is an output from the light receiving portion 2 per time, Vmax is an average value of the output V(t) from the light receiving portion 2 concerning a portion where the colorant is absent, and Vmin is an average value in a state in which the colorant adheres and the output V(t) from the light receiving portion 2 is saturated.

Here, the formula above is designed to compensate for the deterioration and the like of the surface to be measured M.

In addition, as a preferable method of using the photodetector of the dual-wavelength beam system shown in, for example, FIG. 1B, it is possible to cite a method in which a result of photodetection is determined on the basis of information S(t) in which division processing is effected in accordance with $$S(t) = VA(t)/VB(t)$$

where VA(t) is an output from the light receiving portion 2 per time concerning the light of the wavelength (e.g., the light of the wavelength A) applied to the surface to be measured M, and VB(t) is an output from the light receiving portion 2 per time concerning the light of the wavelength (e.g., the light of the wavelength B) not applied to the surface to be measured M.

In this method of use, processing in accordance with "S(t)=VA(t)/VB(t)" means that a change in the transmittance of the light guiding member 3 is canceled, and that only a change in the detected light from the surface to be measured M is extracted.

Consequently, it becomes possible to compensate for variations in the transmittance of the light guiding member 3 and increase the detection accuracy.

Furthermore, as another method of using the photodetector of the dual-wavelength beam system, it is possible to cite the following method: In an image forming apparatus for forming a visible image using a colorant on an image carrying body at the time of using the photodetector shown in FIG. 1B as a device for detecting an amount of the colorant of the visible image on the image carrying body, a result of photodetection is determined on the basis of information S(t) in which arithmetic processing is effected in accordance with $$S(t) = \{VA \max - VA(t)\} / [\{VA \max - VA \min\} VB(t) / VBini]$$

where VA(t) is an output from the light receiving portion 2 per time concerning the light of the wavelength (e.g., the light of the wavelength A) applied to the surface to be measured M, VAmax is an average value of the output VA(t) from the light receiving portion 2 concerning a portion where the colorant is absent, VAmin is an average value in a state in which the colorant adheres and the output VA(t) from the light receiving portion 2 is saturated, VB(t) is an output from the light receiving portion 2 per time concerning the light of the wavelength (e.g., the light of the wavelength B) not applied to the surface to be measured M, and VBini is an initial setting of the output VB(t) of the light receiving portion 2.

This formula is intended to cancel a change in the transmittance of the light guiding member 3 and correct the deterioration of the surface to be measured M.

Furthermore, the invention is not limited to the above-described photodetector and the above-described method of using the same, but is also directed to an image forming apparatus itself incorporating the above-described photodetector.

In this case, according to the invention, it suffices if the photodetector shown in FIG. 1A or FIG. 1B is used as a device for detecting an amount of a colorant of a visible image on an image carrying body in the image forming apparatus for forming the visible image using the colorant on the image carrying body.

Referring now to the accompanying drawings, a detailed description will be given of the embodiments of the invention.

First Embodiment

Figure 2A:
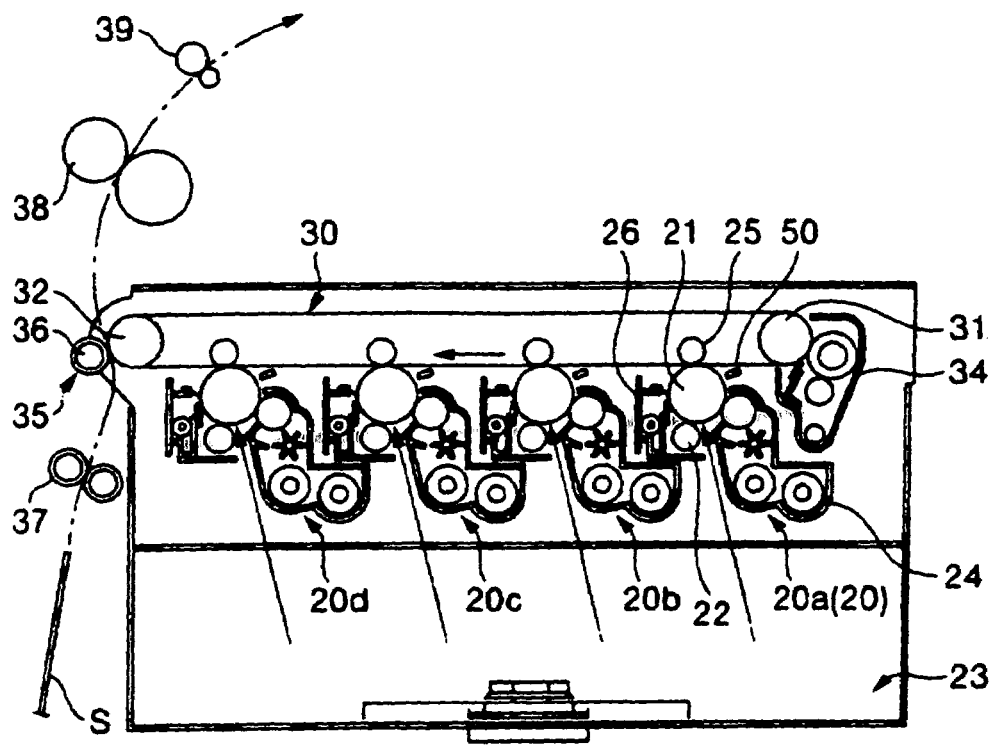
FIG. 2A is an explanatory diagram illustrating an example of an image forming apparatus incorporating a first embodiment of the photodetector (sensor) in accordance with the invention.

FIG. 2A shows an image forming apparatus incorporating a toner amount detector (photodetector) in accordance with a first embodiment of the invention.

In this embodiment, the image forming apparatus is a tandem machine of an intermediate transfer type, and has four image forming units 20 (specifically, 20a to 20d) for forming toner images of respective color components (in this example, toner images of yellow, magenta, cyan, and black). An intermediate transfer belt 30 is disposed at a position opposite to the image forming units 20.

In this embodiment, each image forming unit 20 adopts the electrophotographic system, for example, and has a photoconductor drum 21, which rotates in a predetermined direction. The following are disposed around this photoconductor drum 21: a charger 22 such as a charging roller; an exposure unit 23 such as a laser scanner for writing an electrostatic latent image; a developing unit 24 accommodating each color component toner to form the electrostatic latent image on the photoconductor drum 21 into a visible image; a primary transfer unit 25 such as a primary transfer roller for transferring the toner image on the photoconductor drum 21 onto the intermediate transfer belt 30; and a cleaning unit 26 for cleaning the residual toner on the photoconductor drum 21.

It should be noted that, in this example, the exposure unit 23 is used in common for the respective image forming units 20, and the primary transfer unit 25 is disposed on the rear surface side of the intermediate transfer belt 30.

In addition, in this embodiment, the intermediate transfer belt 30 is stretched between a plurality of stretching rollers 31 and 32, for example. The intermediate transfer belt 30 circulatingly rotate in a predetermined direction by using, for example, one stretching roller 31 as a drive roller.

Further, a secondary transfer unit 35 is disposed downstream of the image forming unit 20d located on the most downstream side of the intermediate transfer belt 30.

In this secondary transfer unit 35, a secondary transfer roller 36 is disposed in face-to-face relation to the stretching roller 32, which is used as a backup roller. A predetermined transfer bias is applied to, for instance, the secondary transfer roller 36, and the stretching roller 32 is grounded, so as to electrostatically transferring the toner image on the intermediate transfer belt 30 onto a recording material S.

It should be noted that reference numeral 34 denotes a belt cleaner for cleaning the residual toner on the intermediate transfer belt 30.

Furthermore, in this embodiment, a recording-material transporting system has a recording-material transporting passage, which is directed in an upward direction from below. Specifically, after the recording material S fed from an unillustrated recording-material supplying tray is positioned by registration rollers 37, the recording material S is transported to a secondary transfer position at a predetermined timing. Subsequently, after the toner image, which has been secondarily transferred onto the recording material S, is fixed by a fixing unit 38, the recording material S is discharged to an unillustrated discharge tray by discharge rollers 39.

Figure 2B:
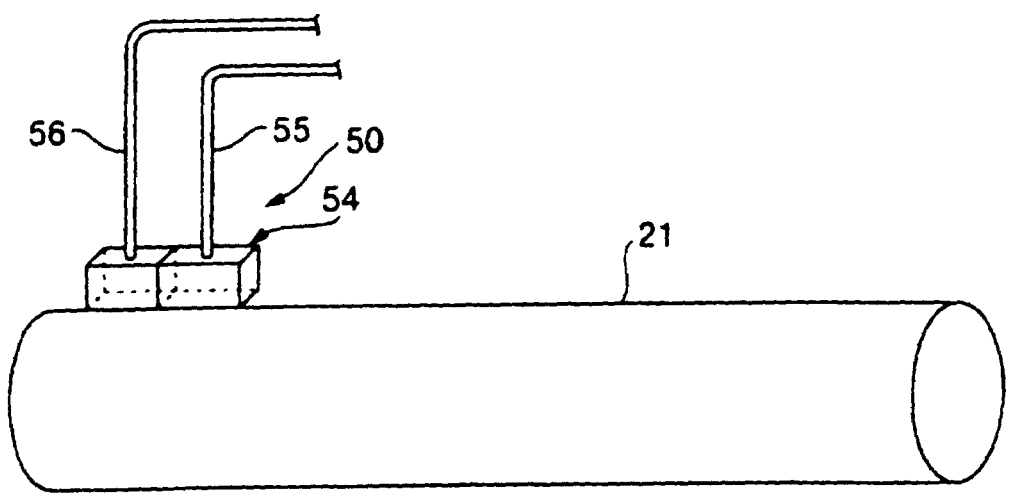
FIG. 2B is an explanatory diagram illustrating an outline of that photodetector.

In particular, in this embodiment, a toner amount detector (photodetector) 50 is disposed in face-to-face relation to the photoconductor drum 21 upstream of the primary transfer position of the photoconductor drum 21 and downstream of the developing position thereof, as shown in FIGS. 2A and 2B.

The basic principle of the measurement by this toner amount detector 50 can be applied to both the reflected-light detection system and the scattered-light detection system. In this example, an example of the construction of the reflected-light detection system is shown.

Figure 3:
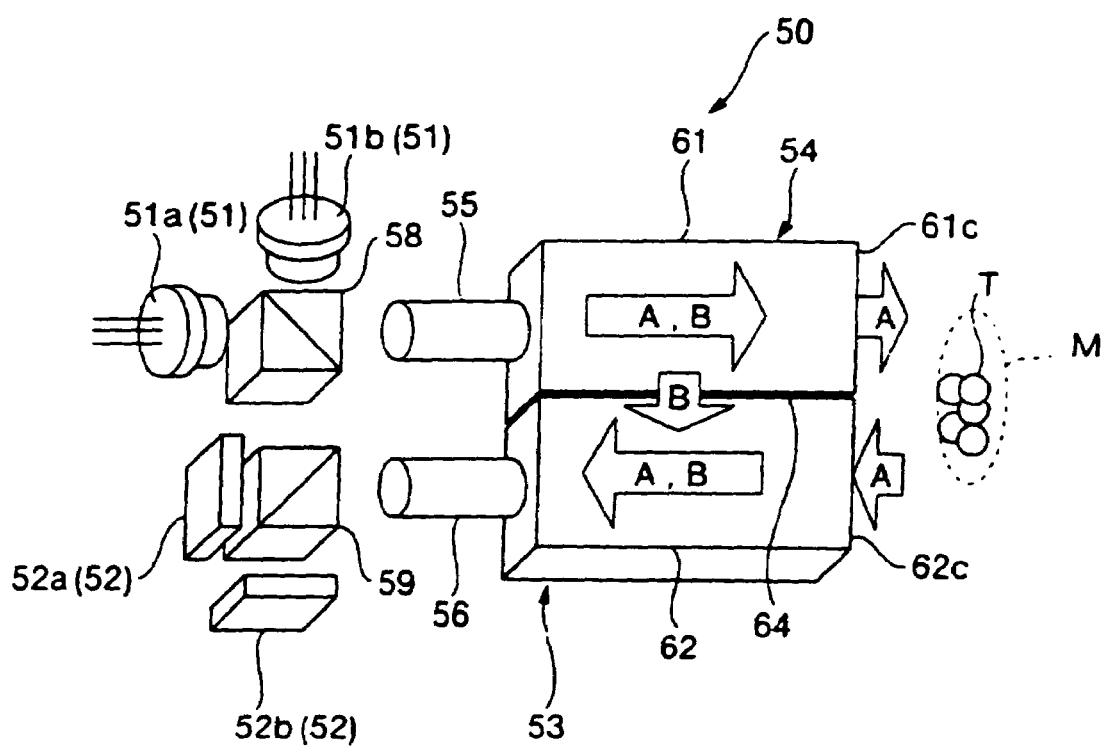
FIG. 3 is an explanatory diagram illustrating the details of the photodetector in accordance with the first embodiment of the invention.

To give a more specific description, as shown in FIGS. 2B and 3, the toner amount detector 50 includes a pair of light emitting elements 51 (specifically 51a and 51b), a pair of light receiving elements 52 (specifically 52a and 52b), and a light guiding member 53. The pair of light emitting elements 51 emit light of different wavelengths A and B, respectively. The pair of light receiving elements 52 detects the light of the different wavelengths A and B, respectively.

The light guiding member 53 is disposed between the light emitting element 51 pair and the light receiving element 52 pair. The light guiding member 53 is adapted to apply the light of one wavelength (A) of the light of two kinds A and B from the light emitting elements 51 to a surface to be measured M. The light guiding member 53 guides the detected light (in this example, reflected light) from the surface to be measured M to one light receiving element 52. On the other hand, the light guiding member 53 guides the light of the other wavelength (B) to the other light receiving element 52 without applying the light of the other wavelength (B) to the surface to be measured M.

It should be noted that, in this example, the light emitting elements 51 (51a, 51b) and the light receiving elements 52 (52a, 52b) are respectively disposed so that the light-applying direction or the light-detecting direction is substantially perpendicular to these elements.

In this embodiment, the light guiding member 53 includes an optical sheet bus 54, an incident-side optical fiber 55, an output-side optical fiber 56, an incident-side beam splitter 58, and an output-side beam splitter 59. The optical sheet bus 54, i.e., a sheet-like optical transmission medium, is disposed in face-to-face relation to the surface to be measured M. The incident-side optical fiber 55 is connected to an incident portion of the optical sheet bus 54. The output-side optical fiber 56 is connected to an output portion of the optical sheet bus 54. The incident-side beam splitter 58 guides the light of the two kinds A and B from the light emitting elements 51 (51a, 51b) to the incident-side optical fiber 55. The output-side beam splitter 59 separates the light of the two kinds A and B from the output-side optical fiber 56 for the light receiving elements 52 (52a, 52b).

Figure 4A:
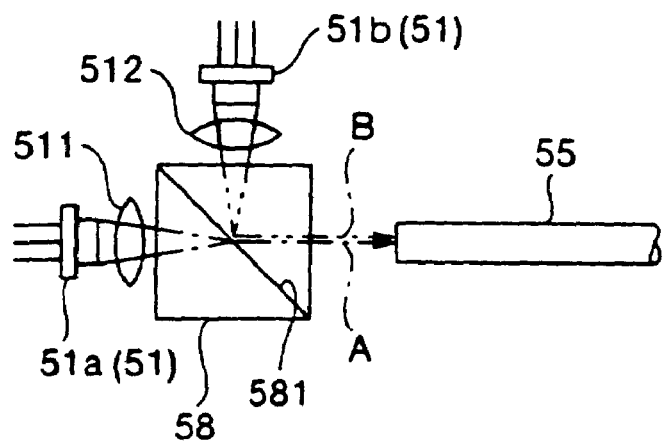
FIG. 4A is an explanatory diagram illustrating a light emitting portion and its vicinities in accordance with the first embodiment.

Here, as shown in FIG. 4A, the incident-side beam splitter 58 is adapted to guide the light of the two kinds A and B from the light emitting elements 51 (51a, 51b) to an inclined reflecting surface 581, which is inclined, for example, substantially 45° with a predetermined transmittance (or reflectivity). The light of one wavelength (A) is transmitted through the inclined reflecting surface 581 as it is, while the light of the other wavelength (B) is reflected thereby, so as to guide the light of the two kinds in the same direction.

It should be noted that focusing lenses 511 and 512 for focusing the light are each provided between the respective light emitting element 51 (51a, 51b) and the incident-side beam splitter 58.

Figure 4B:
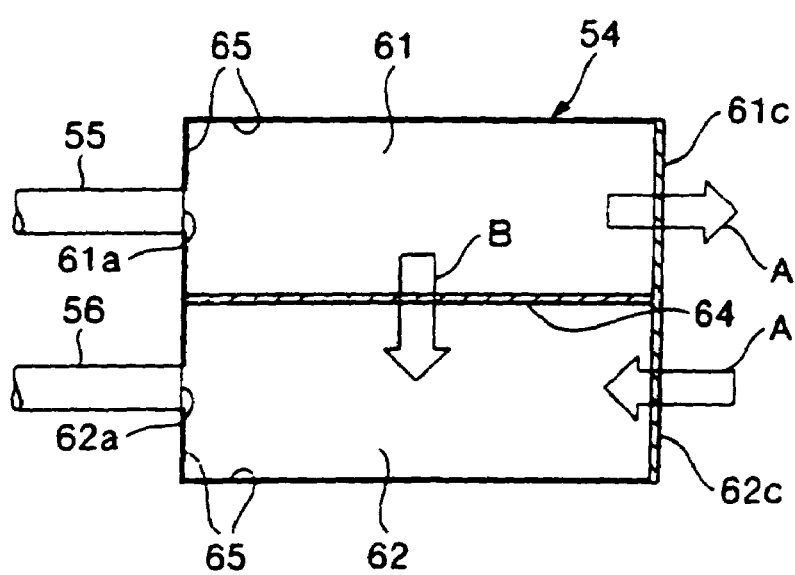
FIG. 4B is an explanatory diagram illustrating an optical sheet bus and its vicinities in accordance with the first embodiment.
Figure 4C:
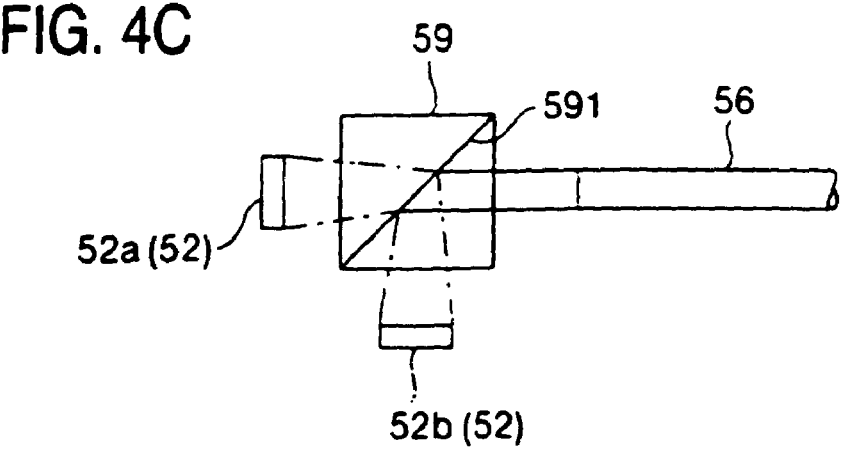
FIG. 4C is an explanatory diagram illustrating a light receiving portion and its vicinities in accordance with the first embodiment.

In addition, as shown in FIG. 4C, the output-side beam splitter 59 is adapted to guide the light of the two kinds A and B from the output-side optical fiber 56 to an inclined reflecting surface 591, which is inclined, for example, substantially 45° with a predetermined transmittance (reflectivity). The light of one wavelength (A) is transmitted through the inclined reflecting surface 591 as it is so as to be guided to one light receiving element 52a. On the other hand, the light of the other wavelength (B) is reflected thereby so as to be guided to the other light receiving element 52b.

In addition, in this embodiment, as shown in FIG. 4B, the optical sheet bus 54 is constructed so that two sheet bus pieces 61 and 62 each having a thickness of, for example, about 0.1 mm to about 2.0 mm are joined with their one end faces adjoining each other. The incident-side optical fiber 55 is connected to an incident portion 61a of the incident-side sheet bus piece 61, while the output-side optical fiber 56 is connected to an output portion 62b of the output-side sheet bus piece 62.

Figure 5:
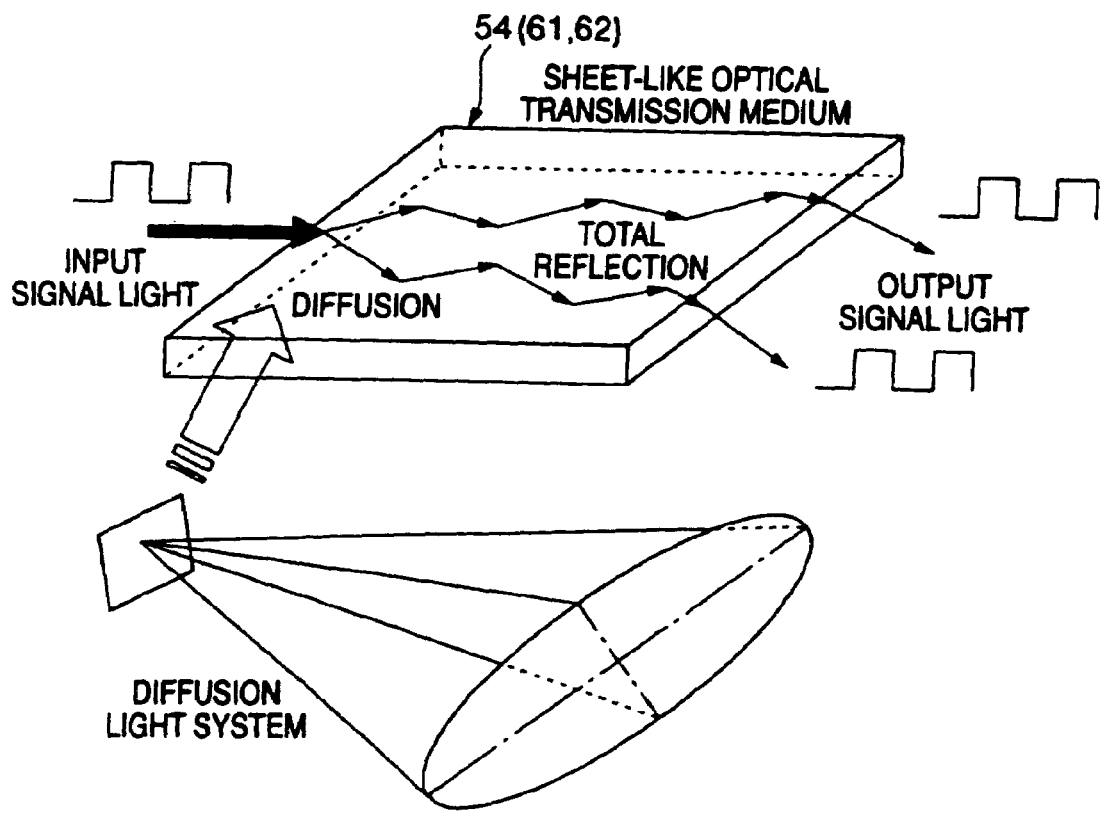
FIG. 5 is a schematic diagram illustrating the basic principle of optical transmission of the optical sheet bus used in the first embodiment.

As shown in FIGS. 4B and 5, the sheet bus pieces 61 and 62 are formed in sheet shape, and diffusively propagate input signal light while repeating total reflection at their internal end faces.

In particular, in this embodiment, the sheet bus pieces 61 and 62 respectively have optical apertures 61c and 62c, through which only the light of one wavelength (A) is transmitted, at their end faces opposite to the surface to be measured M. The optical apertures 61c and 62c are set so that the light is applied to the surface to be measured M through the optical aperture 61c and the detected light (reflected light) from the surface to be measured M is received through the optical aperture 62c. Further, a reflection treated portion 64 for transmitting only the light of the other wavelength (B) is provided at a junction between the two sheet bus pieces 61 and 62.

Here, the optical apertures 61c and 62c and the reflection treated portion 64 can be formed by providing wavelength-dependent coatings, for example.

Further, total-reflection treated portions 65 are provided at the other end faces and sheet surfaces of the sheet bus pieces 61 and 62.

Next, a description will be given of the operation of the toner amount detector in accordance with this embodiment.

Now, the light of the two kinds A and B of different wavelengths is guided from the light emitting elements 51 (51a, 51b) to the incident-side optical fiber 55 by the incident-side beam splitter 58, and is transmitted to the optical sheet bus 54.

At this time, the light of the two wavelengths A and B is transmitted to the incident-side sheet bus piece 61 of the optical sheet bus 54. Of the light of wavelengths A and B, the light of one wavelength (A) is applied to the surface to be measured M through the optical aperture 61c, and the reflected light from the toner T on that surface to be measured M is received by the optical aperture 62c of the output-side sheet bus piece 62.

Meanwhile, the light of the other wavelength (B) is not applied to the surface to be measured M, but is transmitted to the output-side sheet bus piece 62 through the reflection treated portion 64 formed at the junction between the sheet bus pieces 61 and 62.

Consequently, the detected light (reflected light), which are the light of one wavelength (A) from the surface to be measured M and the light of the other wavelength (B) not applied to the surface to be measured M, are both transmitted to the output-side sheet bus piece 62. The light of both wavelengths A and B is guided to the output-side optical fiber 56.

Subsequently, the light of the two wavelengths A and B, which is passed through the output-side optical fiber 56, is separated again into the light of the respective wavelengths (A, B) by the output-side beam splitter 59, and is then made incident upon the light receiving elements 52 (52a, 52b).

Here, if photodiodes are used as the light receiving elements 52 (52a, 52b), each of these photodiodes converts the received quantity of light linearly into a voltage.

At this time, product of information on the light quantity variation corresponding to presence or absence of the toner amount and an amount of variation of the transmittance of the optical fibers 55 and 56 appears in the light of one wavelength (A). Meanwhile, the amount of variation of the transmittance of the optical fibers 55 and 56 appears in the light of the other wavelength (B).

Figure 6A:
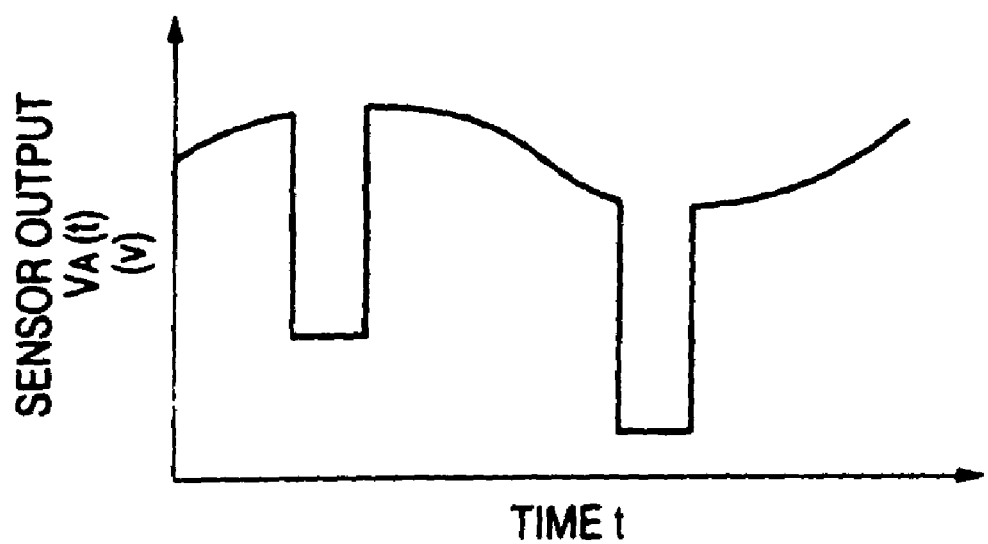
FIG. 6A is an explanatory diagram illustrating an example of a sensor output VA(t)
Figure 6B:
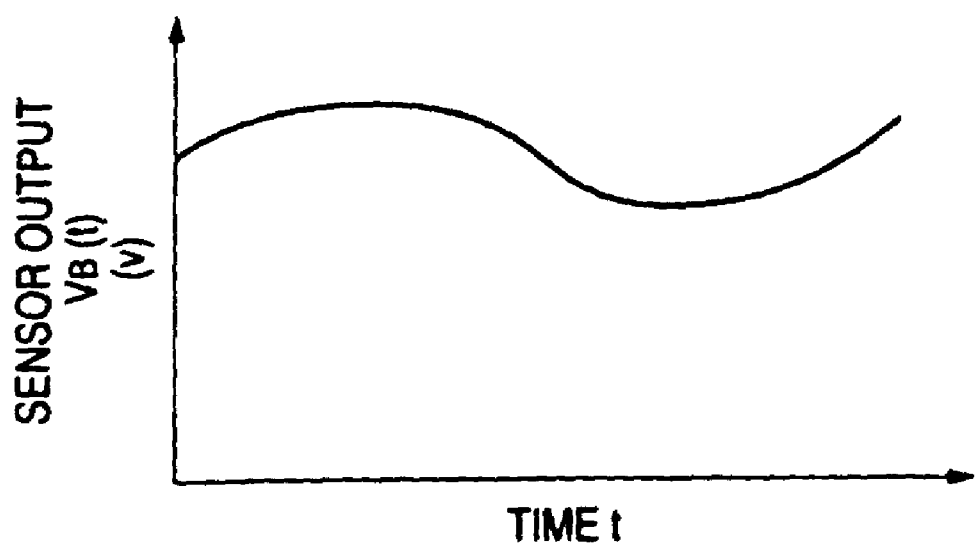
FIG. 6B is an explanatory diagram illustrating an example of a sensor output VB(t)

For this reason, if it is assumed that an output from the light receiving element 52a, which receives the light of one wavelength (A), is VA(t), and that an output from the light receiving element 52b, which receives the light of the other wavelength (B), is VB(t), it is possible to obtain output characteristics shown in FIGS. 6A and 6B.

In this state, when an arithmetic processing (division processing) shown in the following formula (1) is performed so that the output of the light of one wavelength (A) is divided by the output of the light of the other wavelength (B), it is possible to eliminate the effect of the variation of the transmittance of the optical fibers 55 and 56. Thus it is possible to obtain a sensor output value S(t) corresponding to the toner on the surface to be measured M.

$$S(t)=VA(t)/VB(t) \quad (1)$$

It should be noted that the evaluation of the performance of the toner amount detector in accordance with this embodiment is substantiated by an embodiment, which will be described later.

In addition, in this embodiment, the optical sheet bus 54 corresponding to a measuring head portion of the toner amount detector, the light emitting elements 51, and the light receiving elements 52 are disposed to be spaced apart from each other. Therefore, an electric circuit system for the light emitting elements 51 and the light receiving elements 52 can be installed at a position separate from that for the optical sheet bus 54. As the installation space in the vicinity of the surface to be measured M, it is sufficient to secure a narrow space of such a measure as to be capable of installing the optical sheet bus 54.

Further, since the optical system can be simply constructed by the optical fibers 55 and 56 and the optical sheet bus 54 which are inexpensive, it is possible to adopt this embodiment without increasing the cost even in the above-described tandem machine.

Furthermore, if the detection concerning the amounts of toner of the respective colors is effected by staggering the timing for each color, it is possible to jointly use the light emitting elements 51, the light receiving elements 52, a drive circuit board, and the like.

Accordingly, in the case of such a construction, only one set of the light emitting elements 51, the light receiving elements 52, and the drive circuit board may be used. Alternatively, an arrangement may be adopted in which the four image forming units 20 (20a to 20d) are processed by two sets of the light emitting elements 51, the light receiving elements 52, and the drive circuit board.

Second Embodiment

Figure 7A:
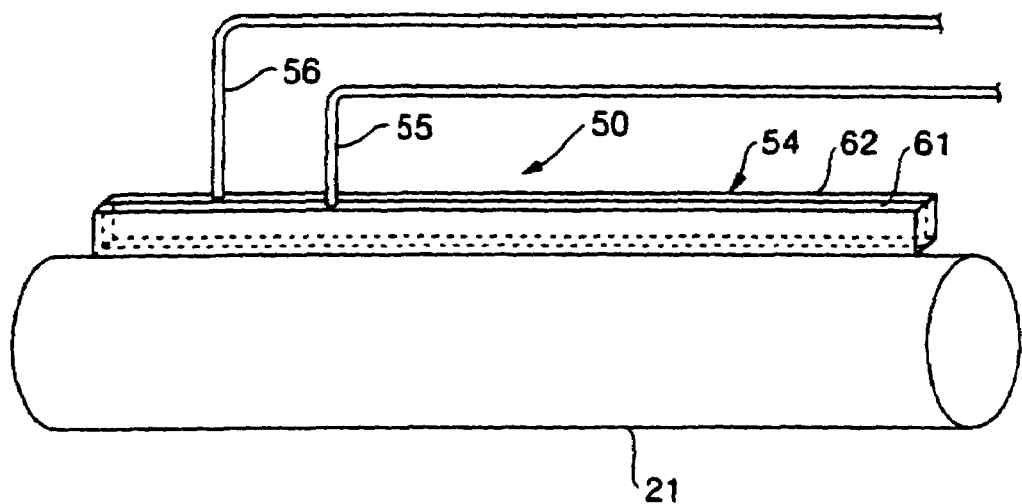
FIG. 7A is an explanatory diagram illustrating an outline of the photodetector in accordance with a second embodiment.
Figure 7B:
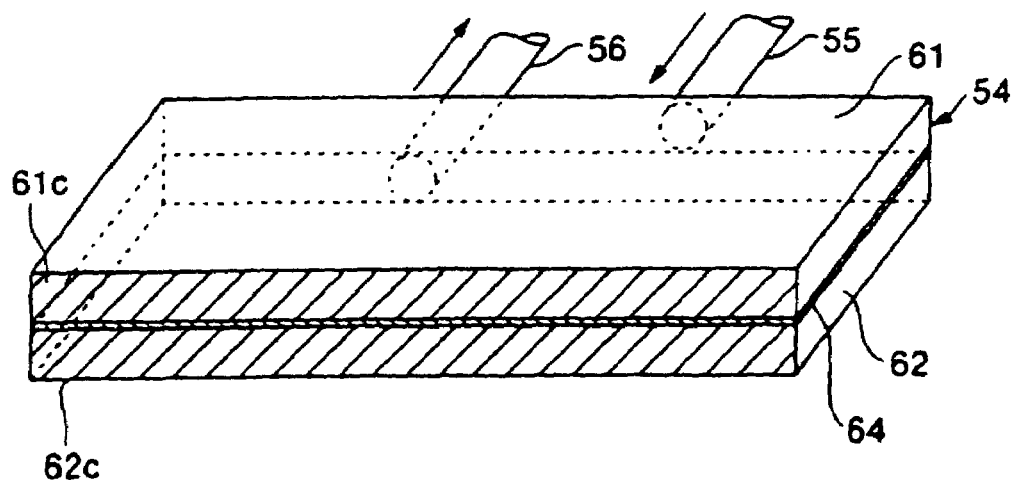
FIG. 7B is a detailed diagram of essential portions thereof.

FIGS. 7A and 7B are explanatory diagrams illustrating an outline of the toner amount detector in accordance with a second embodiment of the invention.

In the drawings, the toner amount detector 50 in terms of its basic construction is substantially similar to that of the first embodiment, but unlike the first embodiment the toner amount detector 50 has an elongated optical sheet bus 54 extending in the axial direction of the photoconductor drum 21.

In this embodiment, the optical sheet bus 54 is constructed so that the two sheet bus pieces 61 and 62 are laminated in the thickness direction. The optical apertures 61c and 62c capable of transmitting only the light of one wavelength (A) are formed at a position opposite to the surface to be measured (the surface of the photoconductor drum 21). The reflection treated portion 64 for transmitting only the light of the other wavelength (B) is provided at the junction between the two sheet bus pieces 61 and 62. The incident-side optical fiber 55 and the output-side optical fiber 56 are respectively connected to the other end portions away from the optical apertures 61c and 62c.

According to this embodiment, since the elongated optical sheet bus 54 is used, an axially extending portion of the photoconductor drum 21 can be set as the surface to be measured over a wide range.

For this reason, even if a situation occurs in which a portion of the photoconductor drum 21 has deteriorated locally, since the surface to be measured extends over a wide range, the detected light from the surface to be measured is made uniform. Therefore, the local deterioration of the surface to be measured does not substantially affect the detection accuracy of the toner amount detector.

Third Embodiment

Figure 8A:
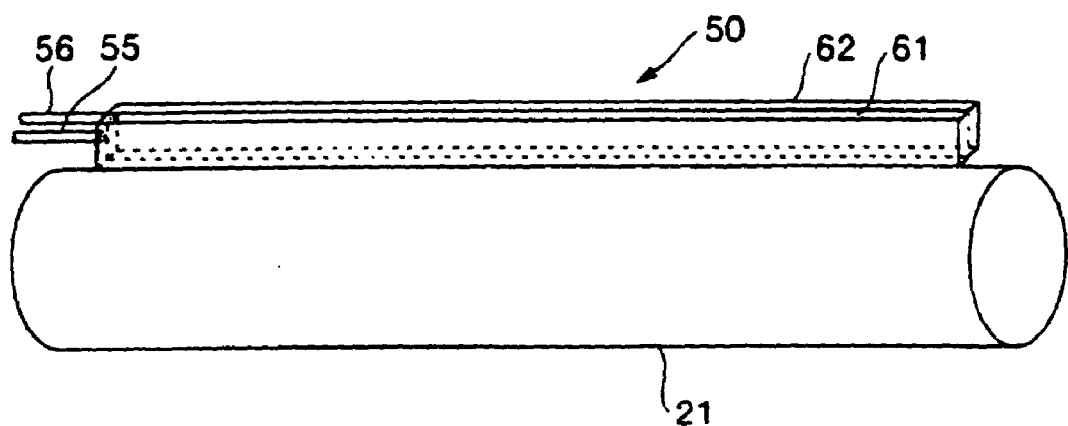
FIG. 8A is an explanatory diagram illustrating an outline of the photodetector in accordance with a third embodiment.
Figure 8B:
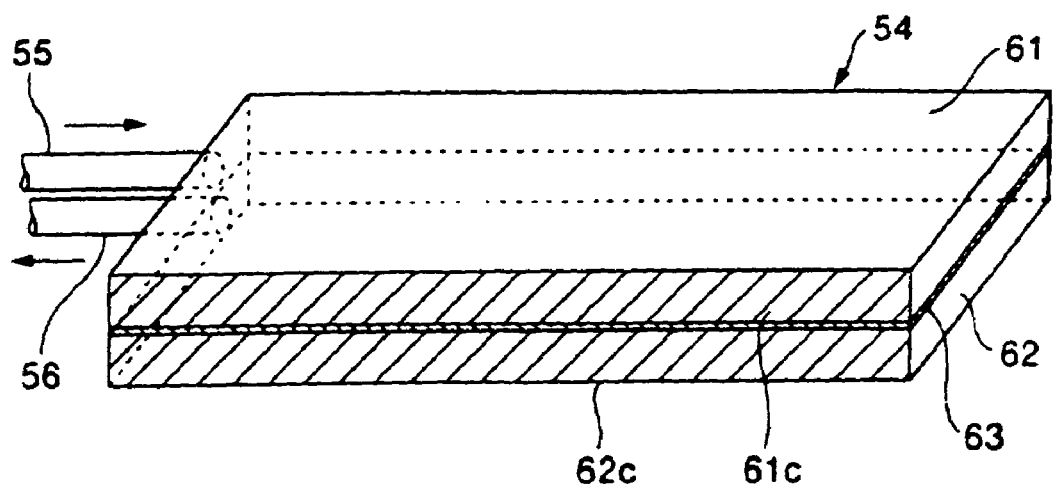
FIG. 8B is a detailed diagram of essential portions thereof.

FIGS. 8A and 8B are explanatory diagrams illustrating an outline of the toner amount detector in accordance with a third embodiment of the invention.

In the drawings, substantially in the same way as the second embodiment, the toner amount detector 50 in terms of its basic construction has the elongated optical sheet bus 54 (having the two sheet bus pieces 61 and 62) extending in the axial direction of the photoconductor drum 21. Unlike the second embodiment, however, the connecting portions of the incident-side optical fiber 55 and the output-side optical fiber 56 are respectively set at portions of the optical sheet bus 54, which are substantially perpendicular to the optical apertures 61c and 62c opposite to the surface to be measured.

It should be noted that those constituent elements that are similar to those of the second embodiment are denoted by the same reference numerals as those of the second embodiment, and a detailed description thereof will be omitted here.

According to this embodiment, since the light from the incident-side optical fiber 55 is diffusively applied along the longitudinal direction of the optical sheet bus 54, it is possible to apply more uniform light to the optical apertures 61c and 62c.

Fourth Embodiment

FIG. 9 shows the toner amount detector in accordance with a fourth embodiment of the invention.

In the drawing, unlike the first embodiment, the toner amount detector 50 is an example of the construction in which the reflected-light detection system and the scattered-light detection system are combined. Specifically, a light guiding member 53 (particularly the optical sheet bus 54), which is different from the first embodiment, is used.

In this embodiment, the optical sheet bus 54 making up the light guiding member 53 is constructed so that three sheet bus pieces 61 to 63 are accommodated within a plane.

Here, the sheet bus piece 61 has the optical aperture 61c serving as a light applying portion, and is set to a thickness and a width of 1 mm and a length of 10 mm, for example.

Further, the pair of sheet bus pieces 62 and 63 are respectively connected to both side ends of the sheet bus piece 61. The sheet bus piece 62 has the optical aperture 62c serving as a specularly-reflected-light detecting portion, and the sheet bus piece 63 has an optical aperture 63c serving as a scattered-light detecting portion.

These optical apertures 61c, 62c, and 63c are provided with reflection treated portions for transmitting only the light of the wavelength A, while the junctions of the sheet bus pieces 61 to 63 are provided with the reflection treated portions 64 for transmitting only the light of the wavelength B.

Further, the incident-side optical fiber 55 is connected to the incident portion of the sheet bus piece 61. Output-side optical fibers 56 and 57 are respectively connected to output portions of the sheet bus pieces 62 and 63.

As for light applied to the surface to be measure M, the specularly reflected light is incident on only the optical aperture 62c of the sheet bus piece 62 due to combination of attachment angles of the sheet bus piece 61 and 62. The specularly reflected light is not incident on the optical aperture 63c of the sheet bus piece 63, and only the scattered light is incident thereon.

In particular, the sheet bus piece 63 is disposed in such a manner as to protrude closer toward the surface to be measured M side than the sheet bus piece 61. This protruding stepped portion 67 serves as a light shielding wall for suppressing the incidence of the specularly reflected light.

Further, two unillustrated light emitting elements are provided in the same way as in the first embodiment, and emitted light are guided to the incident-side optical fiber 55 by an unillustrated beam splitter.

In addition, two unillustrated light receiving elements are provided for each of the output-side optical fibers 56 and 57, and are respectively adapted to detect the light of the two different wavelengths A and B by the unillustrated beam splitter.

Accordingly, according to this embodiment, since the specularly reflected light from the surface to be measured M is detected by the sheet bus piece 62, it is possible to detect the amount of toner by the reflected-light detection system.

Meanwhile, in a case where a color toner has adhered to the surface to be measured M, the toner generates scattered light whose directivity is low. At this time, since the scattered light from the surface to be measured M is detected by the sheet bus piece 63, it is possible to detect the amount of toner by the scattered-light detection system.

Fifth Embodiment

Figure 10:
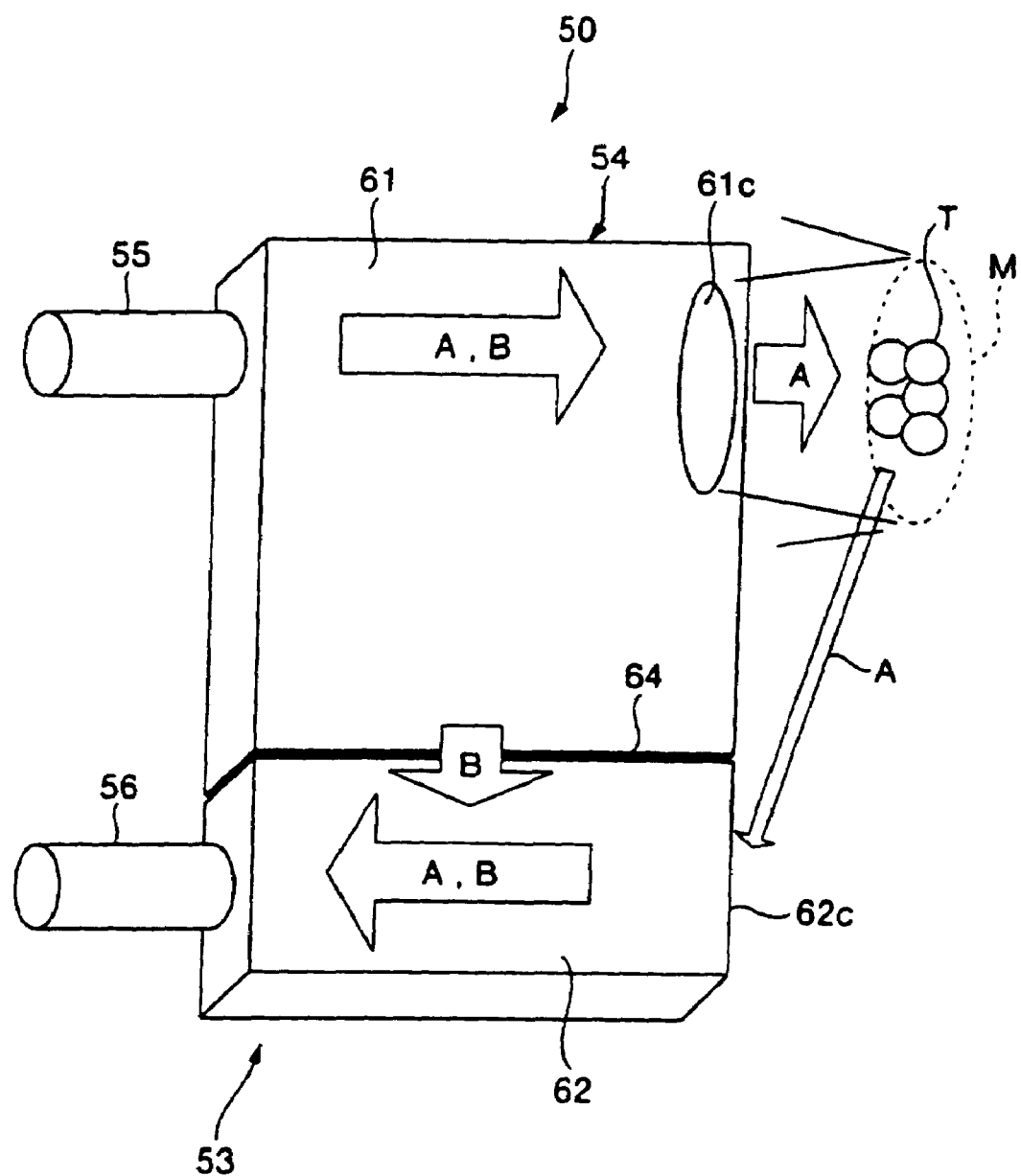
FIG. 10 is an explanatory diagram illustrating an outline of the photodetector in accordance with a fifth embodiment.

FIG. 10 shows the toner amount detector according to a fifth embodiment of the invention.

In the drawing, unlike the first embodiment, the toner amount detector 50 employs the scattered-light detection system. It should be noted that those constituent elements similar to those of the first embodiment will be denoted by the same reference numerals as those of the first embodiment, and a detailed description thereof will be omitted here.

In this embodiment, in the same way as in the first embodiment, the toner amount detector 50 includes unillustrated pair of light emitting elements, unillustrated pair of light receiving elements, and the light guiding member 53 (the optical sheet bus 54, the optical fibers 55 and 56, the unillustrated pair of beam splitters). However, the toner amount detector 50 has an optical sheet bus 54, which is different from that of the first embodiment.

Namely, in this embodiment, the optical sheet bus 54 is constructed so that end portions of the two sheet bus pieces 61 and 62 are joined in a plane. However, the width of the incident-side sheet bus piece 61 is formed to be greater than the width of the output-side sheet bus piece 62. The optical aperture 61c of the incident-side sheet bus piece 61 is formed at a portion spaced apart from the output-side sheet bus piece 62. The optical aperture 62c serving as an optical detection portion is formed at a portion of the output-side sheet bus piece 62 opposite to the surface to be measured M side.

It should be noted that the optical apertures 61c and 62c are transmit only the light of the wavelength A, and the reflection treated portion 64 for transmitting only the light of the wavelength B is formed at the junction between the two sheet bus pieces 61 and 62.

Therefore, according to this embodiment, after the light of the wavelength A guided to the incident-side sheet bus piece 61 is applied to the surface to be measured M through the optical aperture 61c, the scattered light from the surface to be measured M is fetched to the output-side sheet bus piece 62 side, and is transmitted to the light receiving element side together with the light of the wavelength B transmitted through the junction (reflection treated portion 64) between the two sheet bus pieces 61 and 62.

As a result, in signal processing by the light receiving elements, if processing is effected substantially in the same way as in the first embodiment, the amount of toner based on the scattered light can be accurately detected in a state in which the effect of variation in the transmittance of the optical fibers 55 and 56 is eliminated, in the same way as in the first embodiment.

Sixth Embodiment

Figure 11:
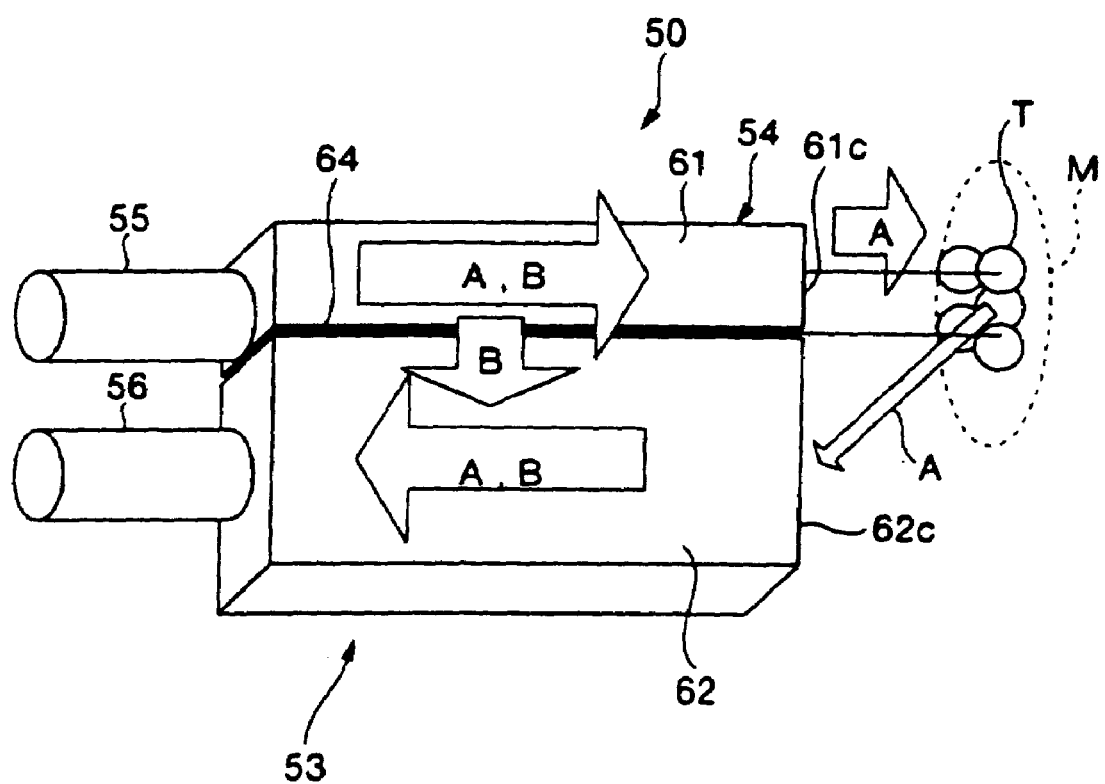
FIG. 11 is an explanatory diagram illustrating an outline of the photodetector in accordance with a sixth embodiment.

FIG. 11 shows the toner amount detector in accordance with a sixth embodiment of the invention.

In the drawing, in the same way as in the fifth embodiment, the toner amount detector 50 employs the scattered-light detection system. Unlike the fifth embodiment, however, the width of the incident-side sheet bus piece 61 of the optical sheet bus 54 is formed to be narrower than that of the output-side sheet bus piece 62, so as to impart directivity to the light applied from the optical aperture 61c of the incident-side sheet bus piece 61 toward the surface to be measured M.

It should be noted that those constituent elements that are similar to those of the fifth embodiment are denoted by the same reference numerals as those of the fifth embodiment, and a detailed description thereof will be omitted here.

According to this embodiment, the light of the wavelength A guided to the incident-side sheet bus piece 61 is applied to the surface to be measured M through the optical aperture 61c.

At this time, since the applied light from the optical aperture 61c has directivity, the specularly reflected light from the surface to be measured M is not directed toward the optical aperture 62c of the output-side sheet bus piece 62, and the scattered light from the surface to be measured M is fetched to the output-side sheet bus piece 62 side.

In addition, this scattered light is transmitted to an unillustrated light receiving element side together with the light of the wavelength B transmitted through the junction (reflection treated portion 64) between the two sheet bus pieces 61 and 62.

As a result, in signal processing by the light receiving elements, if processing is effected substantially in the same way as in the first embodiment, the amount of toner based on the scattered light can be accurately detected in a state in which the effect of variation in the transmittance of the optical fibers 55 and 56 is eliminated, in the same way as in the first embodiment.

Seventh Embodiment

Figure 12:
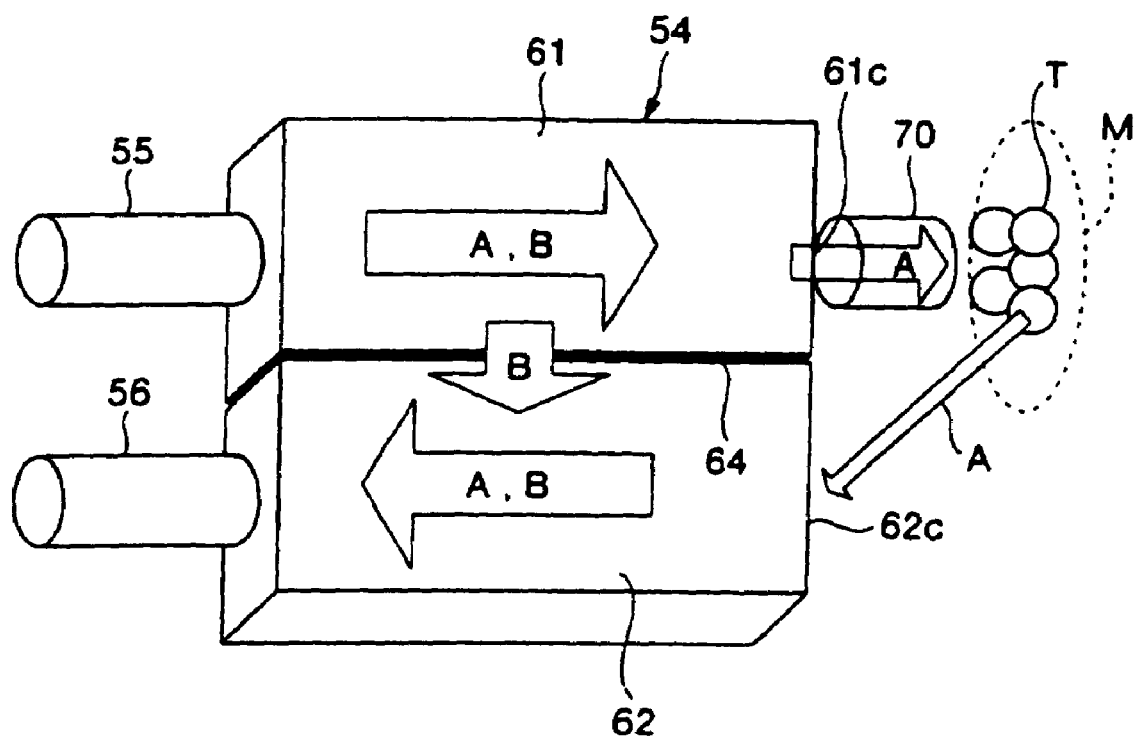
FIG. 12 is an explanatory diagram illustrating an outline of the photodetector in accordance with a seventh embodiment.

FIG. 12 shows the toner amount detector in accordance with a seventh embodiment of the invention.

In the drawing, the toner amount detector 50 is constructed substantially in the same way as in the first embodiment. Unlike the first embodiment, however, the optical aperture 61c of the incident-side sheet bus piece 61 is formed in a narrower state (in this state, spread of light output from the optical aperture 61c is suppressed), and a barrel-like light shielding wall 70 is provided between this optical aperture 61c and the surface to be measured M. It should be noted that those constituent elements that are similar to those of the first embodiment are denoted by the same reference numerals as those of the first embodiment, and a detailed description thereof will be omitted here.

Therefore, according to this embodiment, the light of the wavelength A guided to the incident-side sheet bus piece 61 is applied to the surface to be measured M through the optical aperture 61c and the light shielding wall 70.

At this time, since the specularly reflected light from the surface to be measured M is shielded by the light shielding wall 70, this specularly reflected light is not made incident upon the optical aperture 62c of the output-side sheet bus piece 62, and only the scattered light from the surface to be measured M is fetched to the output-side sheet bus piece 62 side.

For this reason, it is possible to effect the toner amount detection by the scattered-light detection system in the same way as in the fifth and sixth embodiments.

Eighth Embodiment

Figure 13A:
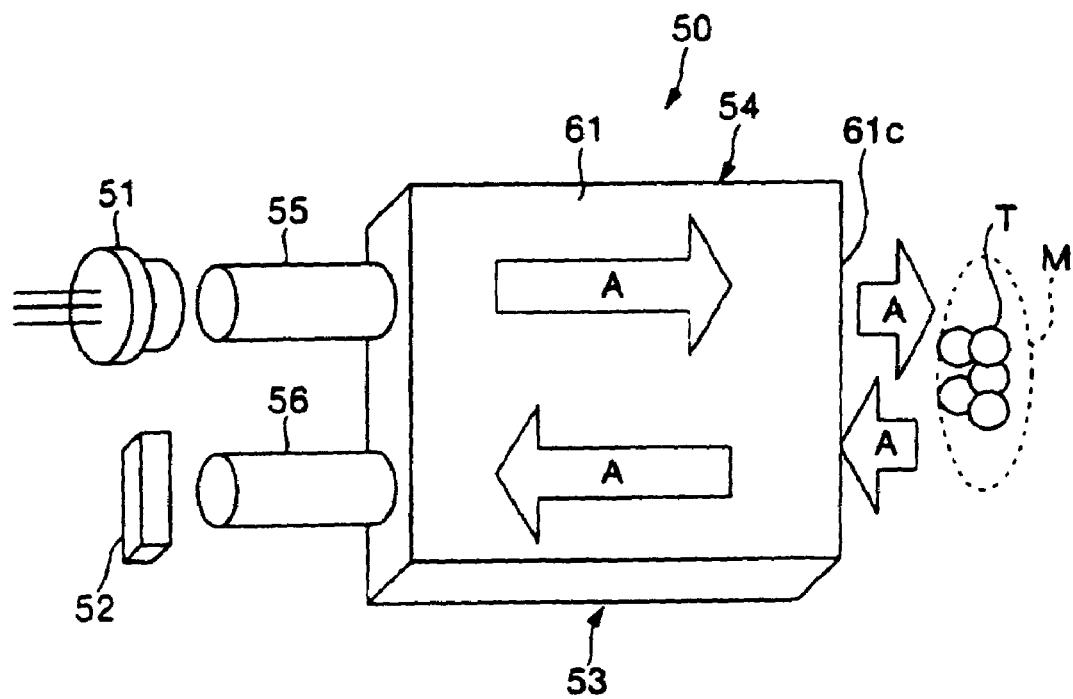
FIG. 13A is an explanatory diagram illustrating an outline of the photodetector in accordance with an eighth embodiment.

FIG. 13A shows the toner amount detector in accordance with an eighth embodiment of the invention.

In the drawing, the toner amount detector is arranged such that, unlike the first to seventh embodiments, the optical sheet bus 54 is formed of a single sheet bus piece 61, and the light of one wavelength A is used.

Here, the optical sheet bus 54 has the optical aperture 61c at one end side of the single sheet bus piece 61. The incident-side optical fiber 55 and the output-side optical fiber 56 are connected to the other end side thereof.

It should be noted that, in this example, the light emitting element 51 is used to apply the light of one wavelength A. The light receiving element 52 also detects the light of one wavelength A.

In this embodiment, the light emitting element 51 emits the light of one wavelength A. The emitted light is transmitted to the optical sheet bus 54 through the incident-side optical fiber 55.

Then, the light is applied from the optical aperture 61c to the surface to be measured M inside this optical sheet bus 54. After the reflected light and the scattered light from the surface to be measured M returns to inside the optical sheet bus 54, the reflected light and the scattered light are superposed on the reflected light occurring in the optical sheet bus 54. Then, the superposed light are transmitted to the light receiving element 52 through the output-side optical fiber 56.

Figure 13B:
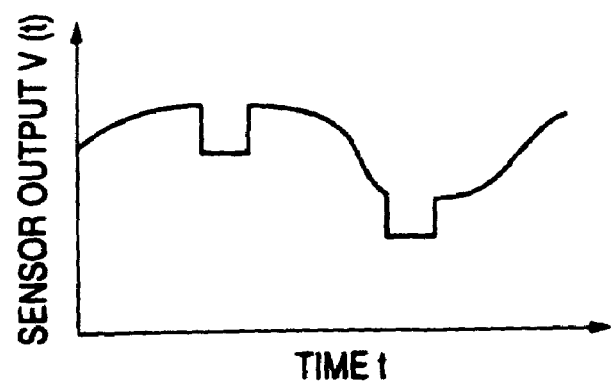
FIG. 13B is an explanatory diagram illustrating an example of the sensor output VA(t) thereof.

An example of the output from this light receiving element 52 is shown in FIG. 13B.

According to this drawing, most of the component of the quantity of light detected by the light receiving element 52 is the reflected light occurring in the optical sheet bus 54, and the component of the information on the presence or absence of the toner is at most about 10%.

For this reason, by processing these two components as shown in Formula (2) below, it is possible to extract the detection signal S(t) representing only the variation due to the amount of toner.

$$S(t) = \{V\max - V(t)\}/\{V\max - V\min\}$$

where V(t) denotes the light receiving portion per time; Vmax denotes the average value of the output V(t) of the light receiving portion from the portion where the toner is absent; and Vmin denotes the average value in a state in which the toner adheres so that the output V(t) of the light receiving element is saturated.

When performing such processing, in the process at a time of actual measurement, a state in which the toner is absent and a toner image having a sufficiently high toner amount are generated on the surface to be measured M and respective values are measured as a preprocess for performing the toner amount measurement.

Further, by measuring the difference between Vmax and V(t) and performing normalization by the difference between Vmax and Vmin, it is possible to offset variations in the quantities of light in the optical fibers 55 and 56.

Ninth Embodiment

Figure 14A:
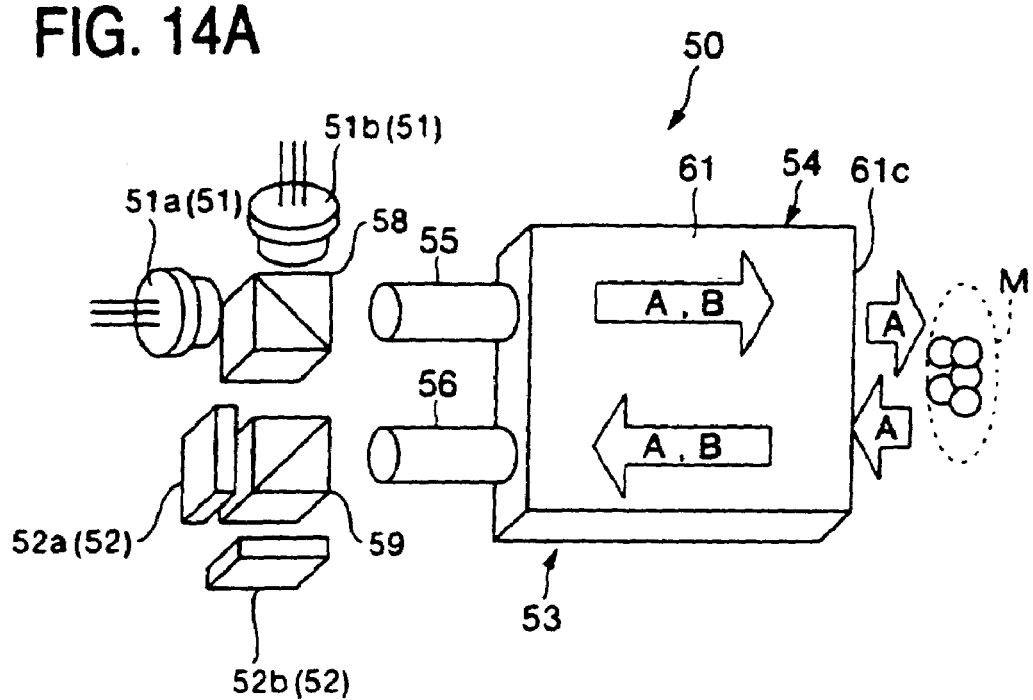
FIG. 14A is an explanatory diagram illustrating an outline of the photodetector in accordance with a ninth embodiment.

FIG. 14A shows a ninth embodiment of the toner amount detector in accordance with the invention.

In the drawing, the toner amount detector 50 is designed to meet the demand that it is undesirable to form an image for reference with a high amount of toner. Unlike the first to seventh embodiments, the optical sheet bus 54 is formed of a single sheet bus piece 61, and the light of different wavelengths A and B is used.

Here, the optical sheet bus 54 has the optical aperture 61c at one end side of the single sheet bus piece 61 for transmitting only the light of one wavelength (A), and the incident-side optical fiber 55 and the output-side optical fiber 56 are connected to the other end side thereof.

It should be noted that, in this example, the light emitting elements 51 (51a, 51b), the light receiving elements 52 (52a, 52b), and the beam splitters 58 and 59 are similar to those of the first embodiment.

Therefore, according to this embodiment, the light of the two wavelengths A and B from the light receiving elements 52 (52a, 52b) is transmitted to the incident-side optical fiber 55 through the incident-side beam splitter 58, and is guided to the optical sheet bus 54.

Figure 14B:
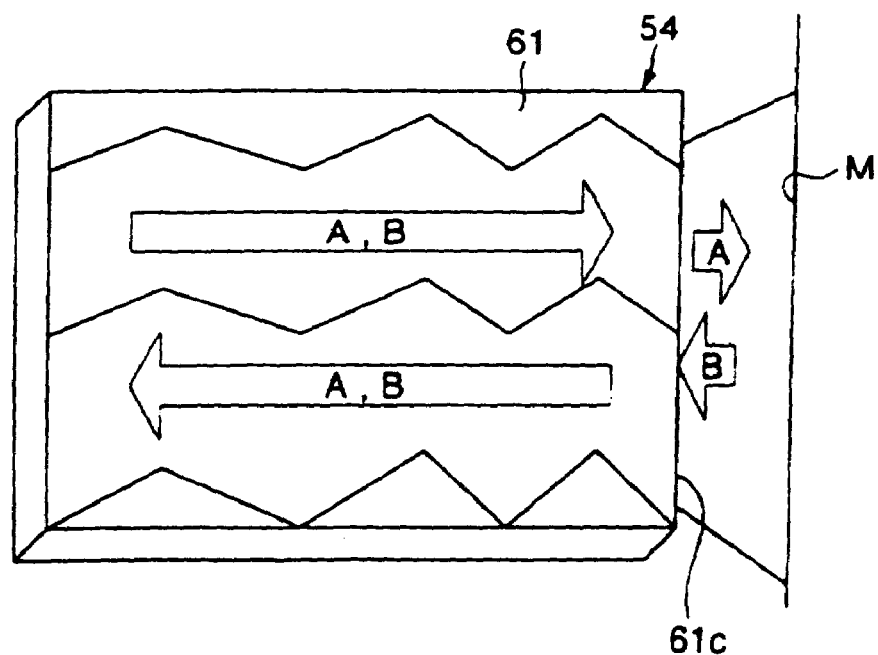
FIG. 14B is an explanatory diagram illustrating the optical sheet bus used in the ninth embodiment.

Then, as shown in FIGS. 14A and 14B, the light is applied from the optical aperture 61c to the surface to be measured M inside this optical sheet bus 54. After the reflected light and the scattered light from the surface to be measured M return to inside the optical sheet bus 54, the reflected light and the scattered light are superposed on the reflected light occurring in the optical sheet bus 54. Then, the superposed light is transmitted through the output-side optical fiber 56. Subsequently, after the light is separated into the light of the respective wavelengths A and B by the output-side beam splitter 59, the light is made incident upon the light receiving elements 52 (52a, 52b).

In the light of the wavelength A, both information on the amount of toner and the amount of variation of the transmittance of the optical fibers 55 and 56 are measured as output values. Meanwhile, in the light of the wavelength B, only the amount of variation of the transmittance of the optical fibers 55 and 56 is measured as an output value.

However, most of the quantity of light of the wavelength A is the reflected light occurring in the optical sheet bus 54, and the component of the information on the presence or absence of the toner is at most about 10%.

By processing these two components as shown in formula (3) below, it is possible to extract the detection signal S(t) representing only the variation due to the amount of toner.

$$S(t) = \{VA\,max - VA(t)\}/[\{VA\,max - VA\,min\}VB(t)/VBini] \quad (3)$$

where VA(t) denotes the output of the light receiving element per time concerning the light of the wavelength (A) applied to the surface to be measured M; VAmax denotes the average value of the output VA(t) of the light receiving element concerning a portion where the toner is absent, VAmin denotes the average value in a state in which the toner adheres and the output VA(t) of the light receiving element is saturated; VB(t) denotes the output of the light receiving element per time concerning the light of the wavelength (B) not applied to the surface to be measured M; and VBini denotes an initial setting value of the output VB(t) of the light receiving element.

10th Embodiment

Figure 15:
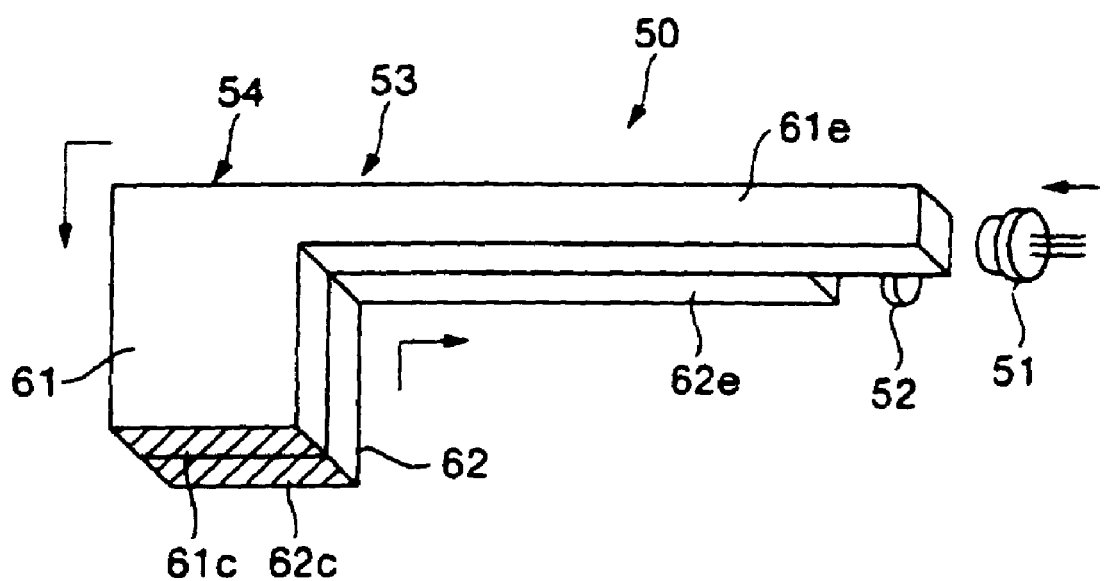
FIG. 15 is an explanatory diagram illustrating an outline of the photodetector in accordance with a 10th embodiment.

FIG. 15 shows the toner amount detector in accordance with a tenth embodiment of the invention.

In the drawing, in the same way as in the first to ninth embodiments, the toner amount detector 50 has the light emitting element 51, the light receiving element 52, and the light guiding member 53 interposed therebetween, but the light guiding member 53 differs from those of the first to ninth embodiments.

In this embodiment, the light guiding member 53 has an optical sheet bus 54 in which, for example, two sheet bus pieces 61 and 62 are joined. The optical apertures 61c and 62c are formed at portions of the respective sheet bus pieces 61 and 62 opposite to the surface to be measured. Meanwhile, an incident-side optical transmission portion 61e is integrally formed at a portion of the sheet bus piece 61, and the light emitting element 51 is disposed at an entrance of this incident-side optical transmission portion 61e. In addition, an output-side optical transmission portion 62e is integrally formed at a portion of the sheet bus piece 62, and the light receiving element 52 is disposed at an exit of this output-side optical transmission portion 62e.

According to this embodiment, it becomes unnecessary to use the optical fibers 55 and 56 such as those shown in the first to ninth embodiments, so that the device configuration can be simplified correspondingly.

EXAMPLE

In this example, the toner amount detector in accordance with the first embodiment was embodied more specifically, and its detection accuracy was examined.

In FIG. 3, laser diodes of the following wavelengths were used as the light receiving elements 52 (52a, 52b):

Wavelength A: 650 nm, 2 mW
Wavelength B: 970 nm, 2 mW

Both of them are easily available, inexpensive laser diodes.

The focusing lenses 511 and 512 (see FIG. 4) respectively focused the light of these two wavelengths (A, B). After the incident-side beam splitter 58 combined the two optical paths, the light was guided to the incident-side optical fiber 55.

The incident-side beam splitter 58 used in this example suffices so long as it is sensitive to the wavelength of the light source (light emitting element 51), and it is possible to use a general one. Here, a mass-produced piece whose transmittance was 50% with respect to both wavelengths A and B was used.

Meanwhile, the optical fiber 55 was made of polycarbonate fiber (PCF), and also suffices so long as it is capable of covering the wavelengths of the light sources (light emitting elements 51).

In addition, the size of the optical fiber 55 was 0.5 mm and presented no hindrance in the wiring in the image forming apparatus, but a connector portion was interposed midway, and the transmittance became 80%±5%. It should be noted that the error portion was the amount of fluctuation of the transmission due to thermal deformation and the like.

Next, a description will be given of the configuration of the optical sheet bus 54.

In this example,

Two sheet bus pieces (61, 62) each having a thickness of 0.5 mm were joined.

The optical sheet bus 54 was configured to be directly coupled to the optical fibers 55 and 56.

The optical sheet bus 54 itself had a transmittance of approximately 100% with respect to the two wavelengths A and B.

The optical apertures (61c, 62c), i.e., end faces on the measuring object side, were provided with coatings for transmitting 400 to 700 nm and reflecting 780 to 970 nm so as to transmit only the light of the wavelength A therethrough.

The junction between the sheet bus pieces 61 and 62 was provided with a coating for transmitting 760 to 1600 nm and reflecting 550 to 650 nm so as to transmit only the light of the wavelength B therethrough.

The reflected light (wavelength A) from the surface to be measured M was 10% at maximum, and the transmitted light at the junction between the sheet bus pieces 61 and 62 was 50%.

The measuring head portion (the optical sheet bus 54 portion) of the toner amount detector constructed as described above was disposed in face-to-face relation to the surface to be measured M. As for the method of installation, it suffices if the measuring head portion is installed substantially perpendicularly with respect to the surface to be measured M, and it is possible to employ a simple method such as bonding with adhesive double coated tape or the like.

The light emitted from the optical sheet bus 54 was guided again to the output-side optical fiber 56.

The transmittance at that time was 80%±5%.

In addition, the light guided by the output-side optical fiber 56 was spectrally separated by the output-side beam splitter 59 provided with a wavelength-dependent coating, and the quantities of the light of the wavelengths A and B are detected by the photodiodes which are the light receiving elements 52 (52a, 52b). At that time, the transmittance of the output-side beam splitter 59 was 50% with respect to both wavelengths A and B.

If the above-described configuration is adopted, it was possible to obtain outputs of:

Wavelength A (information on the presence or absence of the toner was present): 0 to 0.016 mW±13%

Wavelength B (for referencing): 0.08 mW±13%

The error portion based on the variation of the quantity of light (variation of the transmittance of the optical fibers 55 and 56) can be offset by dividing it by the wavelength B, so that the toner amount detector in accordance with the invention can be used for measurement (detection) of sufficiently high accuracy.

Figure 16:
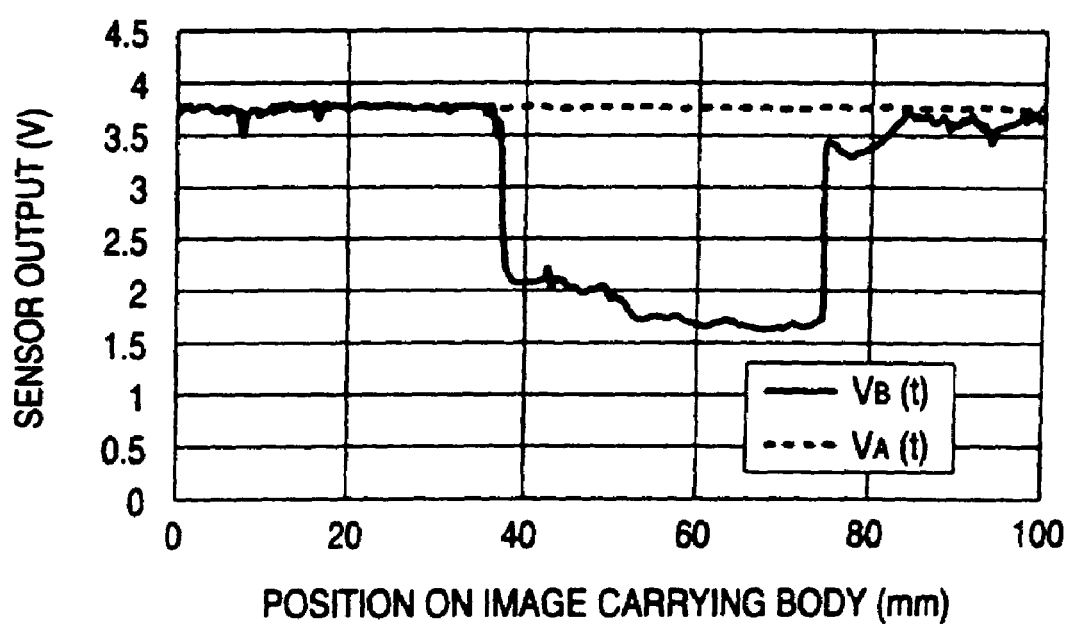
FIG. 16 is an explanatory diagram illustrating examples of the sensor outputs VA(t) and VB(t) in an example.

FIG. 16 shows a specific example of the measurement results obtained in this example.

In this example, the gain was set such that the sensor output averages VAini and VBini were 4 V in a state in which the toner initially did not adhere to the surface to be measured M (photoconductor drum 21).

In contrast, as a result of measuring a certain toner, a decline in the output to 93.7% was noted due to the variation of the transmittance of the optical fibers 55 and 56.

Figure 17:
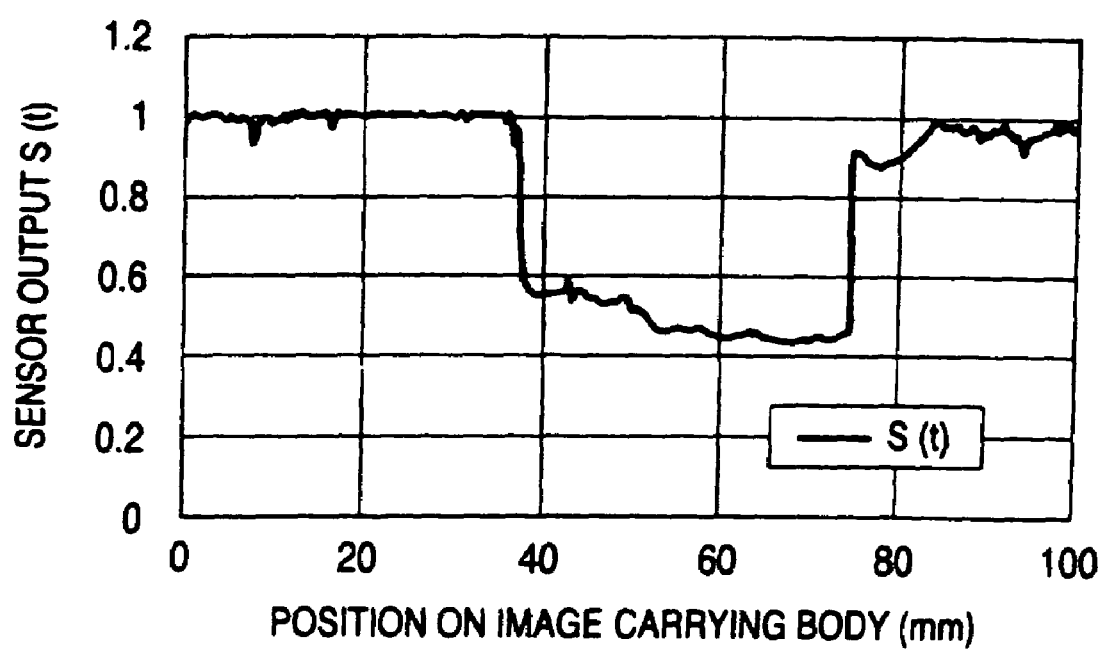
FIG. 17 is an explanatory diagram illustrating an example of a sensor output S(t) after correction in this example.

Results in which this sensor output was corrected are shown in FIG. 17.

Figure 18:
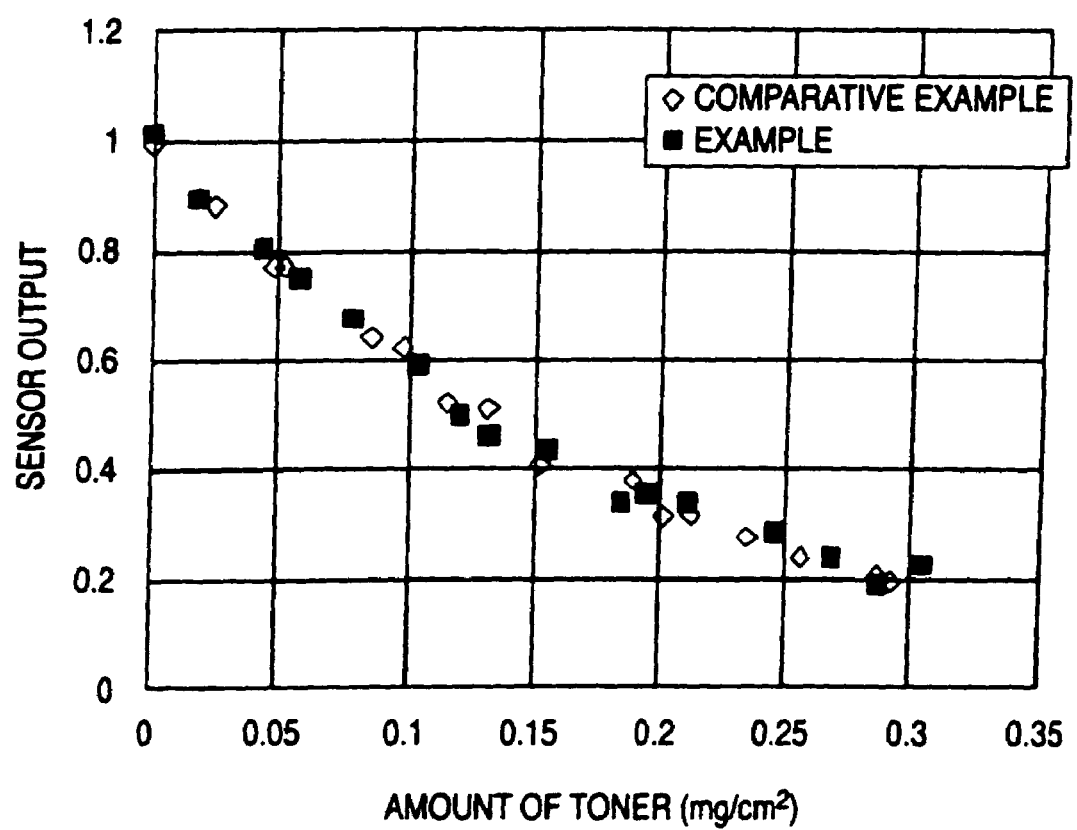
FIG. 18 is an explanatory diagram illustrating an example of the sensor output with respect to the amount of toner in the example and the comparative example.

In addition, FIG. 18 shows the rearrangement of the relationship between the toner amount of the toner and the sensor output by the toner amount detector (sensor) 50 in accordance with this example.

Figure 19A:
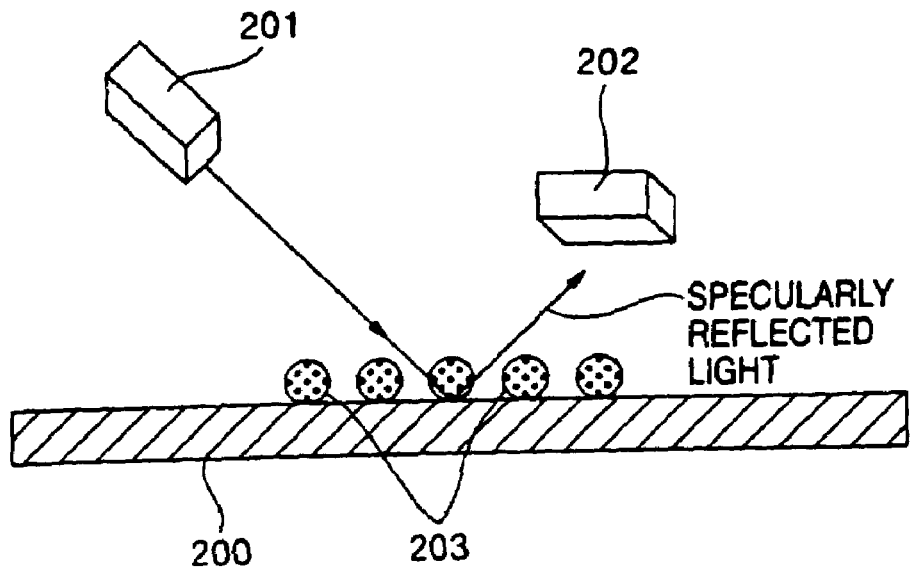
FIG. 19A is an explanatory diagram illustrating an outline of a reflected-light detection system.
Figure 19B:
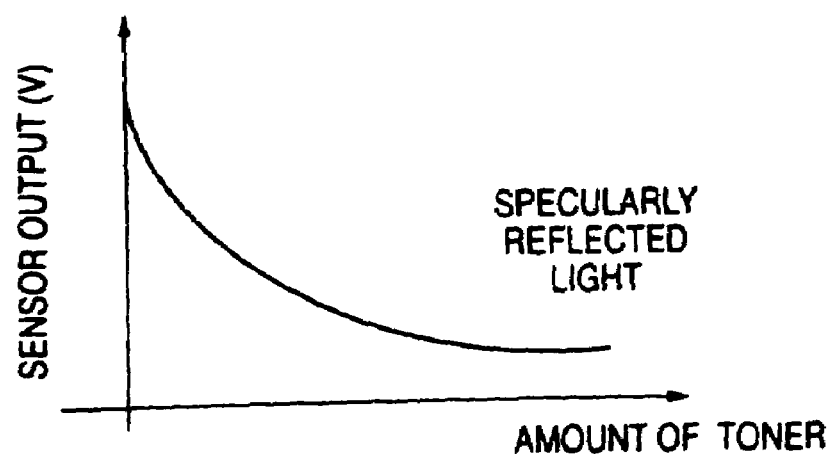
FIG. 19B is an explanatory diagram illustrating sensor output characteristics thereof.
Figure 20A:
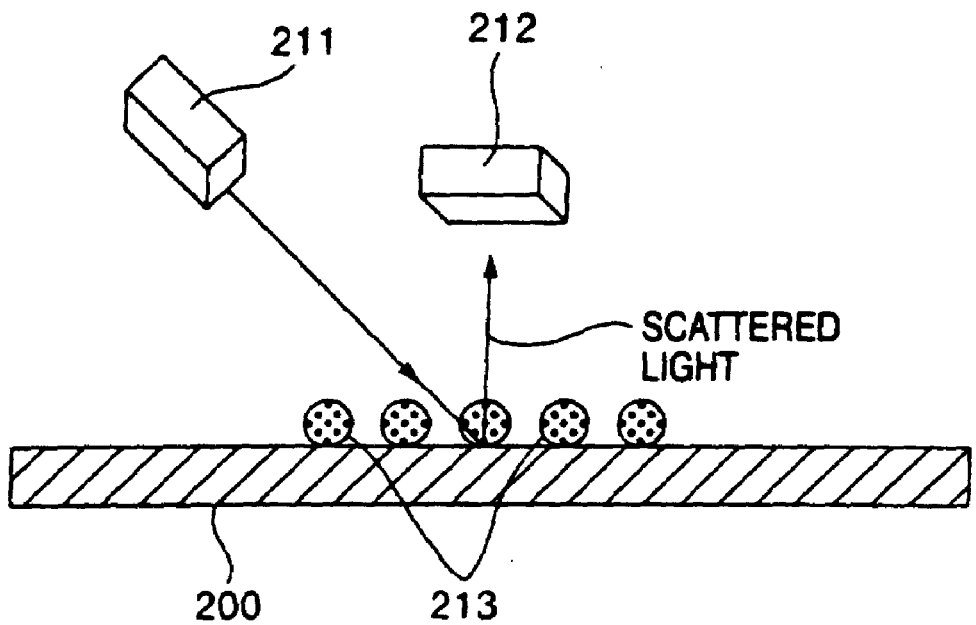
FIG. 20A is an explanatory diagram illustrating an outline of a scattered-light detection system.
Figure 20B:
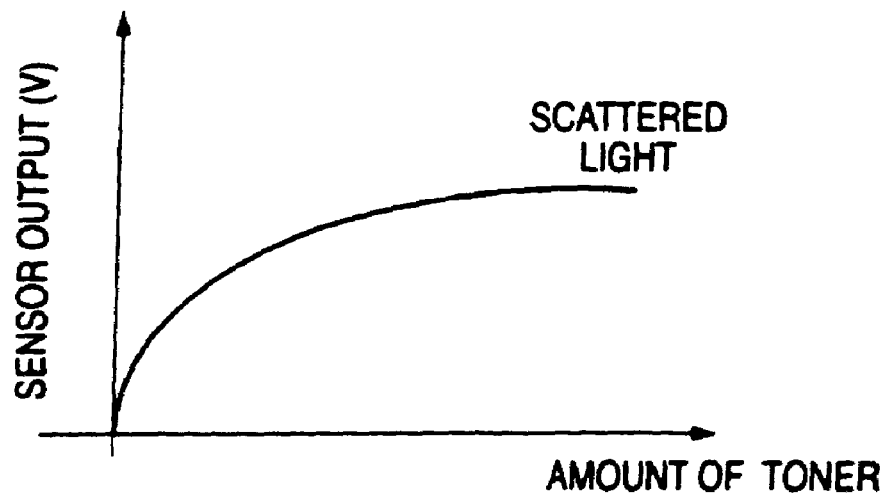
FIG. 20B is an explanatory diagram illustrating sensor output characteristics thereof.
Figure 21:
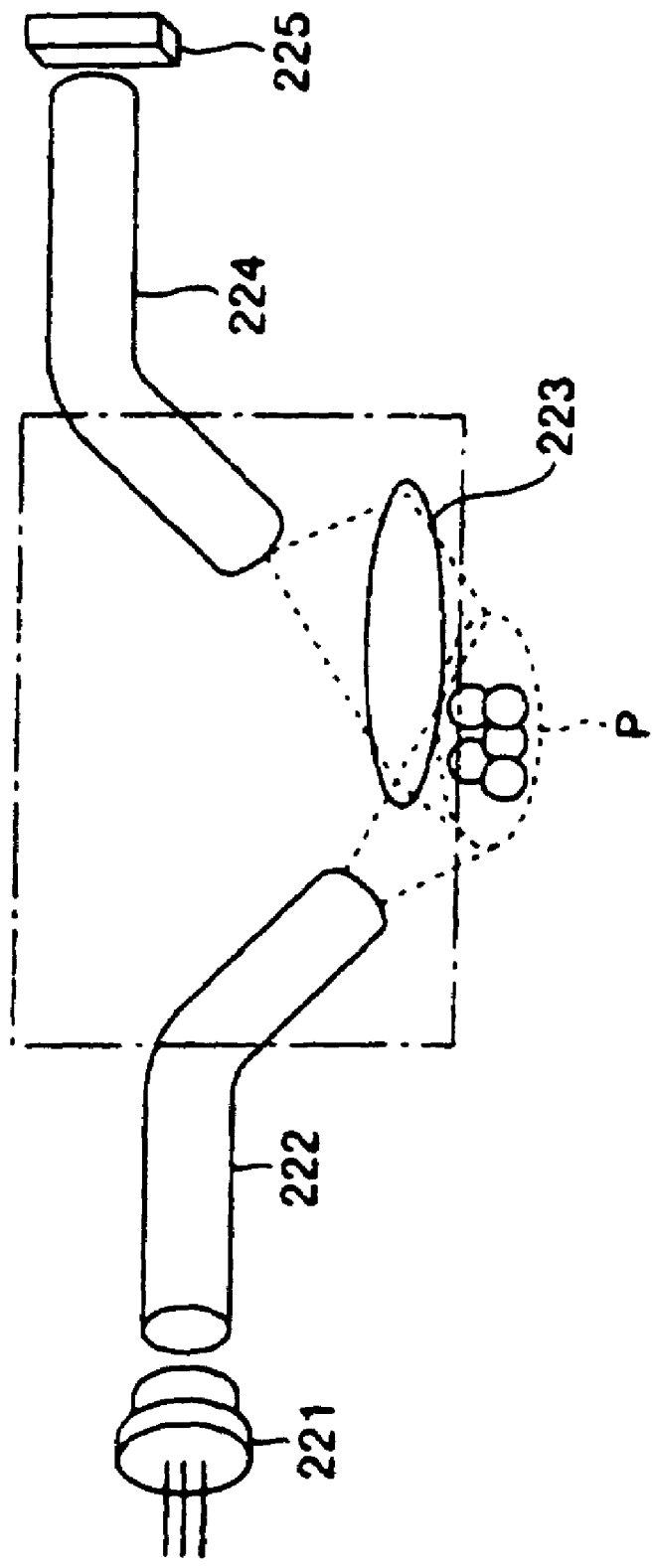
FIG. 21 is an explanatory diagram illustrating an outline of a conventional photodetector.

At this time, when an examination was made on the toner amount and the sensor output in a comparative example (a toner amount detector adopting the system shown in FIG. 19), substantially the same results were obtained between this example and the comparative example.

Thus, in accordance with this example, the toner amount detector in terms of its size can be configured with a thickness of 1 mm, and can be sufficiently used in an image forming apparatus having a dense configuration.

As described above, according to the photodetector in accordance with the invention, since the light guiding member is disposed between the light emitting portion and the light receiving portion, and the sheet-like optical transmission medium is disposed at a portion of this light guiding member opposite to the surface to be measured, it is possible to secure the surface to be measured widely and reliably focus the detected light from the surface to be measured.

For this reason, as compared with a conventional photodetector which focuses the detected light from a spot-like measuring point, it is possible to reduce the effect of the deterioration of the surface to be measured and faulty focusing of the detected light. Thus, it is possible to effectively prevent a decline in the detection accuracy.

In addition, according to another form of the photodetector in accordance with the invention, the light guiding member is disposed between the light emitting portion and the light receiving portion. This light guiding member has optical-transmission-path separating member for allowing only the light of one wavelength of the light of the two kinds from the light emitting portion to be applied to the surface to be measured, and for allowing the detected light from the surface to be measured to be guided to the light receiving portion together with the light of another wavelength. Therefore, the "detected light from the surface to be measured plus the component of variation of the transmittance of the light guiding member" can be detected from the light of one wavelength, while the "component of variation of the transmittance of the light guiding member" can be detected from the light of the other wavelength.

For this reason, it becomes possible to cancel variations in the transmittance of the light guiding member, and it is possible to accurately detect only the detected light from the surface to be measured.

Accordingly, it is possible to effectively prevent a decline in the detection accuracy due to the variation of the transmittance of the light guiding member.

Further, at the time of using the photodetector in accordance with the invention, if consideration is given to the characteristics of the surface to be measured itself, it is possible to effectively prevent the effect of the deterioration of the surface to be measured. Therefore, the detection accuracy can be maintained more favorably correspondingly.

Furthermore, at the time of using the photodetector of the dual-wavelength beam system in accordance with the invention, if the variation of the transmittance of the light guiding member is canceled, it is possible to accurately detect only the detected light from the surface to be measured. Therefore, the detection accuracy can be maintained more favorably correspondingly.

In addition, according to the image forming apparatus in accordance with the invention, the use of a photodetector of high detection accuracy makes it possible to accurately detect the amount of a colorant accompanying the image formation. Therefore, it is readily possible to realize the image formation of high image quality.

What is claimed is:

1. A photodetector for detecting at least one of light reflected from a surface to be measured and light scattered from the surface to be measured, comprising:
a light emitting portion for emitting light;
a light receiving portion for sensing light; and
a light guiding member for substantially totally reflecting the light thereinside to guide the light from the light emitting portion to the surface to be measured, and substantially totally reflecting detection light thereinside to guide the detection light from the surface to be measured to the light receiving portion,
wherein the light guiding member has a sheet-shaped optical transmission medium disposed at a portion facing to the surface to be measured and transmitting the light by internal reflection, and including an optical aperture spaced from and facing to the surface to be measured,
wherein the sheet-shaped optical transmission medium includes a light applying portion for applying the light to the surface to be measured and a light detecting portion for detecting the light from the surface to be measured as the optical aperture;
wherein the sheet-shaped optical transmission medium is a plurality of sheet-shaped optical transmission media; and
wherein the light applying portion and the light detecting portion are formed in different parts of the sheet-shaped optical transmission medium.

2. The photodetector according to claim 1, wherein the light guiding member includes:
an incident-side optical transmission member for forming an optical transmission path between the light emitting portion and an incident portion of the sheet-shaped optical transmission medium; and
an output-side optical transmission member for forming an optical transmission path between an output portion of the sheet-shaped optical transmission medium and the light receiving portion.

3. The photodetector according to claim 1,
wherein the sheet-shaped optical transmission medium includes a light applying portion for applying the light to the surface to be measured and a light detecting portion for detecting the light from the surface to be measured as the optical aperture; and
wherein the light detecting portion allows specularly reflected light from the surface to be measured to be incident thereon.

4. A photodetector for detecting light reflected or scattered from a surface to be measured, comprising:
a light emitting portion for emitting the light of two kinds of different wavelengths;
a light receiving portion for sensing the light of the two kinds of different wavelengths; and
a light guiding member,
wherein the light guiding member includes an optical-transmission-path separating member for applying light of one of the two kinds from the emitting portion to the surface to be measured and guiding light to be detected from said surface to be measured together with light of the other one of the two kinds to the light receiving portion;
wherein the light guiding member is disposed at a portion facing to the surface to be measured;
wherein the light guiding member includes a sheet-shaped optical transmission medium, which transmits the light by inside reflection and has an optical aperture facing to the surface to be measured;
wherein the optical-transmission-path separating member is disposed in the sheet-shaped optical transmission medium; and
wherein the optical-transmission-path separating member applies said light of said one kind through the optical aperture to the surface to be measured, fetches reflected or scattered light from the surface to be measured, and does not apply light of the other one of said two kinds through the optical aperture to external.

5. The photodetector according to claim 4,
wherein the light guiding member includes:
an incident-side optical transmission member for guiding the light of the two kinds from the light emitting portion to an incident portion of the sheet-shaped optical transmission medium; and
an output-side optical transmission member for guiding the light of the two kinds output from an output portion of the sheet-shaped optical transmission medium to corresponding sensing portions of the light receiving portion, respectively.

6. The photodetector according to claim 4,
wherein the optical aperture is coated with reflection coating having wavelength dependency;
wherein light of one of the two kinds can transmit the reflection coating; and
wherein light of the other of the two kinds can be reflected at the reflection coating.

7. The photodetector according to claim 4,
wherein the sheet-shaped optical transmission medium includes a light applying portion for applying the light to the surface to be measured and a light detecting portion for detecting the light from the surface to be measured as the optical aperture;
wherein the sheet-shaped optical transmission medium is a plurality of sheet-shaped optical transmission media;
wherein the light applying portion and the light detecting portion are formed in different parts of the sheet-shaped optical transmission medium;
wherein a junction between the plurality of sheet-shaped optical transmission media is coated with reflection coating;
wherein light of said one of the two kinds can be reflected at the reflection coating; and
wherein light of said other one of the two kinds can transmit the reflection coating.

8. An image forming apparatus for forming visible image using a color material on a image carrying body, the image forming apparatus comprising:
a detector for detecting the color material of the visible image on the image carrying body, the detector including:
a light emitting portion for emitting the light of two kinds of different wavelengths, respectively;
a light receiving portion for sensing the light of the two kinds of different wavelengths, respectively; and
a light guiding member,
wherein the light guiding member includes an optical-transmission-path separating member for applying light of one of the two kinds from the emitting portion to the surface to be measured and guiding light to be detected from said surface to be measured together with light of the other one of the two kinds to the light receiving portion;
wherein the light guiding member is disposed at a portion facing to the surface to be measured;

wherein the light guiding member includes a sheet-shaped optical transmission medium, which transmits the light by inside reflection and has an optical aperture facing to the surface to be measured;

wherein the optical-transmission-path separating member is disposed in the sheet-shaped optical transmission medium; and wherein the optical-transmission-path separating member applies said light of said one kind through the optical aperture to the surface to be measured, fetches reflected or scattered light from the surface to be measured, and does not apply light of the other one of said two kinds through the optical aperture to external.

9. The photodetector according to claim 1, wherein the light emitting portion, the light receiving portion and the light guiding member are separate from each other.

* * * * *